US008703145B2

(12) United States Patent
Yamamoto

(10) Patent No.: US 8,703,145 B2
(45) Date of Patent: Apr. 22, 2014

(54) MATERIALS AND METHODS FOR IMMUNIZING AGAINST FIV INFECTION

(75) Inventor: Janet K. Yamamoto, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 422 days.

(21) Appl. No.: 12/575,058

(22) Filed: Oct. 7, 2009

(65) Prior Publication Data

US 2010/0111899 A1    May 6, 2010

Related U.S. Application Data

(63) Continuation of application No. 10/844,658, filed on May 12, 2004, now abandoned.

(60) Provisional application No. 60/470,066, filed on May 12, 2003.

(51) Int. Cl.
*A61K 39/21* (2006.01)
*A61K 38/19* (2006.01)
*A61K 38/20* (2006.01)

(52) U.S. Cl.
USPC ............... 424/188.1; 424/187.1; 424/85.2

(58) Field of Classification Search
CPC ............ A61K 39/21; A61K 2039/515; A61K 2039/525; A61K 2039/555; A61K 2039/55522; C07K 14/005; C12N 2740/15022; C12N 2740/15034; C12N 2740/16022
See application file for complete search history.

(56) References Cited

U.S. PATENT DOCUMENTS

| | | | |
|---|---|---|---|
| 4,861,720 A | 8/1989 | Pedersen et al. | |
| 5,037,753 A | 8/1991 | Pedersen et al. | |
| 5,118,602 A | 6/1992 | Pedersen et al. | |
| 5,275,813 A | 1/1994 | Yamamoto et al. | |
| 5,401,628 A | 3/1995 | Chiodi | |
| 5,510,106 A | 4/1996 | Yamamoto et al. | |
| 5,530,101 A | 6/1996 | Queen et al. | |
| 5,565,319 A | 10/1996 | Pedersen et al. | |
| 5,585,089 A | 12/1996 | Queen et al. | |
| 5,693,762 A | 12/1997 | Queen et al. | |
| 5,700,469 A | 12/1997 | McMichael et al. | |
| 5,763,160 A | 6/1998 | Wang | |
| 5,766,598 A | 6/1998 | Paoletti et al. | |
| 5,846,546 A | 12/1998 | Hurwitz et al. | |
| 5,846,825 A | 12/1998 | Yamamoto | |
| 5,849,533 A | 12/1998 | Berman et al. | |
| 6,107,077 A | 8/2000 | Yamamoto | |
| 6,180,370 B1 | 1/2001 | Queen et al. | |
| 6,254,872 B1 | 7/2001 | Yamamoto | |
| 6,407,213 B1 | 6/2002 | Carter et al. | |
| 6,447,993 B1 | 9/2002 | Yamamoto | |
| 6,500,623 B1 | 12/2002 | Tung | |
| 6,503,753 B1 | 1/2003 | Rios | |
| 6,544,528 B1 | 4/2003 | Yamamoto | |
| 7,311,921 B2 | 12/2007 | Yamamoto | |
| 7,658,927 B2 * | 2/2010 | Yamamoto | 424/184.1 |
| 2001/0004531 A1 | 6/2001 | Sung et al. | |
| 2002/0032165 A1 | 3/2002 | Johnson et al. | |
| 2002/0156037 A1 | 10/2002 | Volkin et al. | |
| 2003/0104611 A1 | 6/2003 | Johnston et al. | |
| 2003/0223964 A1 | 12/2003 | Barnett et al. | |
| 2004/0009941 A1 | 1/2004 | Johnson et al. | |
| 2004/0047878 A1 | 3/2004 | Deng et al. | |
| 2004/0076632 A1 | 4/2004 | Deng et al. | |
| 2005/0031639 A1 | 2/2005 | Yamamoto | |

FOREIGN PATENT DOCUMENTS

| | | |
|---|---|---|
| WO | WO 93/01278 | 1/1993 |
| WO | WO 94/20622 | 9/1994 |
| WO | WO 94/28929 A1 | 12/1994 |
| WO | WO 96/30045 | 10/1996 |
| WO | WO 02/067984 A2 | 9/2002 |

OTHER PUBLICATIONS

Uhl et al., Veterinary Immunology and Immunopathology, 2002, 90:113-132.*
Matsuo et al., Journal of General Virology, 1992, 73:2445-2450.*
Elyar et al., Vaccine, 1997, 15(12/13):1437-1444.*
GenBank: ABV82543.1: demonstrates that SEQ ID No. 12 in U.S. Patent 7658927 is HIV1-p24 derived polypeptide.*
Ackley, C. et al. "Immunologic Abnormalities in Pathogen-Free Cats Experimentally Infected with Feline Immunodeficiency Virus" *Journal of Virology*, Nov. 1990, pp. 5652-5655, vol. 64, No. 11.
Felgner, P. et al. "Lipofection: A highly efficient, lipid-medicated DNA-transfection procedure" *Proc. Natl. Acad. Sci. USA*, Nov. 1987, pp. 7413-7417, vol. 84.
Hosie, M. et al. "Serological responses of cats to feline immunodeficiency virus" *AIDS*, 1990, pp. 215-220, vol. 4.
Kakinuma, S. et al. "Nucleotide Sequence of Feline Immunodeficiency Virus: Classification of Japanese Isolates into Two Subtypes Which Are Distinct from Non-Japanese Subtypes" *Journal of Virology*, Jun. 1995, pp. 3639-3646, vol. 69, No. 6.
Louwagie, J. et al. "Phylogenetic analysis of *gag* genes from 70 international HIV-1 isolates provides evidence for multiple genotypes" *AIDS*, 1993, pp. 769-780, vol. 7, No. 6.
Merrifield, R. B. "Solid Phase Peptide Synthesis. I. The Synthesis of a Tetrapeptide" *Amer. Chem. Soc.*, Jul. 20, 1963, pp. 2149-2154, vol. 85.
Murphy, F. et al. "Virus Taxonomy" *Virology*, 1990, pp. 9-35, Chapter 2, 2nd edition, Raven Press, Ltd., New York.

(Continued)

*Primary Examiner* — Louise Humphrey
(74) *Attorney, Agent, or Firm* — Saliwanchik, Lloyd & Eisenschenk

(57) ABSTRACT

The subject invention pertains to methods and compositions for protecting feline animals from infection by FIV using immunogens derived from primate immunodeficiency viruses, including HIV and SIV. Methods for vaccinating feline animals with the subject vaccine compositions are described. Feline animals vaccinated according to the methods and compositions of the subject invention exhibit protective humoral and cellular immune responses to FIV when challenged with FIV.

20 Claims, No Drawings

(56) References Cited

OTHER PUBLICATIONS

Olmsted, R. et al. "Molecular cloning of feline immunodeficiency virus" *Proc. Natl. Acad. Sci. USA*, Apr. 1989, pp. 2448-2452, vol. 86.

Olmsted, R. et al. "Nucleotide sequence analysis of feline immunodeficiency virus: Genome organization and relationship to other lentiviruses" *Pro. Natl. Acad. Sci. USA*, Oct. 1989, pp. 8088-8092, vol. 86.

Pedersen, N. et al. "Isolation of a T-Lymphotropic Virus from Domestic Cats with an Immunodeficiency-Like Syndrome" *Science*, Feb. 13, 1987, pp. 790-793, vol. 235.

Posnett, D. et al. "A Novel Method for Producing Anti-peptide Antibodies" *The Journal of Biological Chemistry*, Feb. 5, 1988, pp. 1719-1725, vol. 263, No. 4.

Pu, R. et al. "Dual-subtype FIV vaccine protects cats against in vivo swarms of both homologous and heterologous subtype FIV isolates" *AIDS*, 2001, pp. 1225-1237, vol. 15.

Rigby, M. A. et al. "Evolution of structural proteins of feline immunodeficiency virus: molecular epidemiology and evidence of selection for change" *Journal of General Virology*, 1993, pp. 425-436, vol. 74.

Sodora, D. et al. "Identification of Three Feline Immunodeficiency Virus (FIV) *env* Gene Subtypes and Comparison of the FIV and Human Immunodeficiency Virus Type 1 Evolutionary Patterns" *Journal of Virology*, Apr. 1994, pp. 2230-2238, vol. 68, No. 4.

Talbott, R. L. et al. "Nucleotide sequence and genomic organization of feline immunodeficiency virus" *Proc. Natl. Acad. Sci. USA*, Aug. 1989, pp. 5743-5747, vol. 86.

Tam, J. "Synthetic peptide vaccine design: Synthesis and properties of a high-density multiple antigenic peptide system" *Proc. Natl. Acad. Sci. USA*, Aug. 1988, pp. 5409-5413, vol. 85.

Whetter, L. et al. "Pathogenesis of simian immunodeficiendy virus infection" *Journal of General Virology*, 1999, pp. 1557-1568, vol. 80.

Yamamoto, J. et al. "Feline Immunodeficiency Syndrome—A Comparison between Feline T-Lymphotropic Lentivirus and Feline Leukemia Virus" *Leukemia*, 1988, pp. 204S-215S, vol. 2, No. 12 Supplement.

Yamamoto, J. et al. "Pathogenesis of experimentally induced feline immonodeficiency virus infection in cats" *American Journal of Veterinary Research*, Aug. 1988, pp. 1246-1258, vol. 49, No. 8.

Byars, N.E. et al. "Adjuvant formulation for use in vaccines to elicit both cell-mediated and humoral immunity" *Vaccine*, Sep. 1987, pp. 223-228, vol. 5.

De Ronde, A. et al. "Antibody Response in Cats to the Envelope Proteins of Feline Immunodeficiency Virus: Identification of an immunodominant Neutralization Domain" *Virology*, 1994, pp. 257-264, vol. 198.

Leutenegger, C. M. et al. "Immunization of Cats against Feline Immunodeficiency Virus (FIV) Infection by Using Minimalistic Immunogenic Defined Gene Expression Vector Vaccines Expressing FIV gp140 Alone or with Feline Interleukin-12 (IL-12), IL-16, or a CpG Motif" *Journal of Virology*, Nov. 2000, pp. 10447-10457, vol. 74, No. 22.

Hosie, M. J. et al. "Protection against Homologous but Not Heterologous Challenge Induced by Inactivated Feline Immunodeficiency Virus Vaccines" *Journal of Virology*, 1995, vol. 69, No. 2, pp. 1253-1255.

Johnson, C. M. et al. "FIV as a Model for AIDS Vaccination" *AIDS Research and Human Retroviruses*, 1994, vol. 10, No. 3, pp. 225-228.

Yamamoto, J. K. et al. "Experimental Vaccine Protection against Homologous and Heterologous Strains of Feline Immunodeficiency Virus" *Journal of Virology*, 1993, vol. 67, No. 1, pp. 601-605.

Yamamoto, J. K. et al. "Experimental Vaccine Protection Against Feline Immunodeficiency Virus" *AIDS Research and Human Retroviruses*, 1991, vol. 7, No. 11, pp. 911-922.

Yamamoto, J. K. et al. "Development of IL-2-Independent Feline Lymphoid Cell Lines Chronically Infected with Feline Immunodeficiency Virus: Importance for Diagnostic Reagents and Vaccines" *Intervirology*, 1991, vol. 32, pp. 361-375.

Okada, S. et al. "Superinfection of Cats with Feline Immunodeficiency Virus Subtypes A and B" *AIDS Research and Human Retroviruses*, 1994, vol. 10, No. 12, pp. 1739-1746.

Satoshi, N. et al. "Establishment of FIV-Producing Cell Lines From FIV Seropositive Cats" V International Conference on AIDS, The Scientific and Social Challenge, 1989, XP-000972975, abstract only, p. 598.

Abimiku, A.G., et al. "HIV-1 recombinant poxvirus vaccine induces cross-protection against HIV-2 challenge in rhesus macaques," *Nat. Med.*, 1995, pp. 321-329, vol. 1.

Altschul, S.F. et al. "Gapped BLAST and PSI-BLAST: A New Generation of Protein Database Search Programs," *Nucl. Acids Res.*, 1997, pp. 3389-3402, vol. 25, No. 17.

Bottiger, B., et al. "Envelope cross-reactivity between human immunodeficiency virus type 1 and 2 detected by different serological methods: correlation between cross-neutralization and reactivity against the main neutralizing site," *J. Virol.*, 1990, pp. 3492-3499, vol. 64, No. 7.

Calarota, S.A., et al. "Present status of human HIV vaccine development," *AIDS*, 2003, pp. S73-S84, vol. 17, Supp. 4.

Cohen, J. "Vaccine results lose significance under scrutiny," *Science*, 2003, p. 1495, vol. 299.

Gaucher, D., et al. "Gerbil interleukin-18 and caspase-1: cloning, expression and characterization," *Gene*, 2003, pp. 159-166, vol. 307.

Greenberg, A.E., et al. "HIV-2 and natural protection against HIV-1 infection," *Science*, 1996, pp. 1959-1960, vol. 272.

Guyader, M., et al. "Genome organization and transactivation of the human immunodeficiency virus type 2," *Nature*, 1987, pp. 662-669, vol. 326.

Henderson, D.A., et al. "Smallpox and vaccinia," In: *Vaccines*, 3rd Ed., 2004, pp. 123-153, Plotkin SA, Orenstein WA (editors). Elsevier Inc., Philadelphia.

Ishizaka, T., A. et al. "Molecular cloning of feline interferon-γ-inducing factor (interleukin-18) and its expression in various tissues," *Vet. Immunol. Immunopathol.*, 2001, pp. 209-218, vol. 79.

Karlin, S. et al. "Methods for Assessing the Statistical Significance of Molecular Sequence Features by Using General Scoring Schemes," *Proc. Natl. Acad. Sci. USA*, 1990, pp. 2264-2268, vol. 87.

Karlin, S. et al. "Applications and Statistics for Multiple High-Scoring Segments in Molecular Sequences," *Proc. Natl. Acad. Sci. USA*, 1993, pp. 5873-5877, vol. 90.

Lerner, D.L., et al. "*Felis catus* interleukin-4 mRNA," NCBI GenBank, 1997 (accession U39634).

Matsuo, K., et al., "Highly conserved epitope domain in major core protein p24 is structurally similar among human, simian and feline immunodeficiency viruses," *J. Gen. Virol.*, 1992, pp. 2445-2450, vol. 73.

McMichael, A.J., et al. "HIV vaccines 1983-2003," *Nat. Med.*, 2003, pp. 874-880, vol. 9.

Murphy, F.A. "Virus Taxonomy," In: *Fundamental Virology*, 3rd Ed., 1996, pp. 15-57, Fields BN, Knipe DM, PM Howley PM (editors). Lippincott, Raven Publishers, Philadelphia.

Nath, M.D., et al. "In vitro assembly of feline immunodeficiency virus capsid protein: biological role of conserved cysteines," *Arch. Biochem. Biophys.*, 2001, pp. 287-294, vol. 392.

Nixon, D.F., et al. "An HIV-1 and HIV-2 cross-reactive cytotoxic T-cell epitope," *AIDS*, 1990, pp. 841-845, vol. 4.

Pu R., et al. "Dual-subtype FIV vaccine (Fel-O-Vax® FIV) protection against heterologous subtype B FIV isolate," *Journal of Feline Medicine & Surgery*, 2005, pp. 65-70, vol. 7, No. 1.

Pu, R., et al. "FIV antigens induce potent cross-reactive immunity to HIV-1," *Experimental Biology 2002*. New Orleans, Apr. 2002 [FASEB Journal, p. A298, Abstract No. 237.21].

Reis E Sousa, C. "Toll-like receptors and dendrite cells: for whom the bug tolls," *Semin. Immunol.*, 2004, pp. 27-34, vol. 16.

Robert-Guroff, M., et al. "Cross-neutralization of human immunodeficiency virus type 1 and 2 and simian immunodeficiency virus isolates," *J. Virol.*, 1992, pp. 3602-3608, vol. 66, No. 6.

Rowland-Jones, S., et al. "HIV-specific cytotoxic T-cells in HIV-exposed but uninfected Gambian women," *Nat. Med.*, 1995, pp. 59-64, vol. 1, No. 1.

(56) References Cited

OTHER PUBLICATIONS

Salek-Ardakani, S., et al. (2002) "High level expression and purification of the Epstein-Barr virus encoded cytokine viral interleukin 10: efficient removal of endotoxin," *Cytokine*, 2002, pp. 1-13, vol. 17, No. 1.

Tanabe, T., et al. "Feline immunodeficiency virus lacks sensitivity to the antiviral activity of feline IFNγ" *J. Interferon Cytokine Res.*, 2001, pp. 1039-1046, vol. 21.

Travers, K., et al. "Natural protection against HIV-1 infection provided by HIV-2," *Science*, Jun. 16, 1995, pp. 1612-1615, vol. 268.

Uhl, E.W., et al. "FIV vaccine development and its importance to veterinary and human medicine: a review," *Vet. Immunol. Immunopath.*, 2002, pp. 113-132, vol. 90.

Schim Van Der Loeff, M.F, et al. "HIV-2 infection does not protect against HIV-1 infection in a rural community in Guinea-Bissau," *AIDS*, 2001, pp. 2303-2310, vol. 15.

Weigel, B.J., et al. "Comparative analysis of murine marrow-derived dendritic cells generated by Flt3L or GM-CSF/IL-4 and matured with immune stimulatory agents on the in vivo induction of antileukemia responses," *Blood*, Dec. 1, 2002, pp. 4169-4176, vol. 100, No. 12.

Wondimu, A., et al. "Molecular cloning, expression and characterization of the *Canis familiaris* interleukin-4," *Cytokine*, Nov. 7, 2001, pp. 88-92, vol. 16, No. 3.

Yamamoto, J.K., B.A. Torres, R. Pu (2002) "Development of the dual-subtype FIV vaccine," *AIDScience* Apr. 2002, 2(8), website at aidscience.org/Articles/AIDScience020.asp/ Accessed Dec. 25, 2004.

De Rozieres, S. et al. "Characterization of a Highly Pathogenic Molecular Clone of Feline Immunodeficiency Virus Clade C" *Journal of Virology*, 2004, vol. 78, No. 17, pp. 8971-8982.

Yazbak, F.E., at al. "Postpartum live virus vaccination: lessons from veterinary medicine," *Med. Hypoth.*, 2002, pp. 280-282, vol. 59.

Zvelebil, M.J., et al. "Predictions of linear T-cell and B-cell epitopes in proteins encoded by HIV-1, HIV-2 and $SIV_{MAC}$ and the conservation of these sites between strains," *FEBS Lett*, Dec. 1988, pp. 9-21, vol. 242.

Coleman, J.K., at al. "HIV-1 p24 Vaccine Protects Cats Against Feline Immunodeficiency Virus Infection," *AIDS*, 2005, pp. 1457-1466, vol. 19.

Norrgren, H., et al. "Trends and interaction of HIV-1 and HIV-2 in Guinea-Bissau, West Africa: no protection of HIV-2 against HIV-1 infection," *AIDS*, 1999, pp. 701-707, vol. 13.

Flynn J.N., et al. "Induction of feline immunodeficiency virus-specific cytotoxic T cells in vivo with carrier-free synthetic peptide" *Journal of Virology*, Sep. 1994, pp. 5835-5844, vol. 68, No. 9.

Nixon D.F., et al. "HIV-! Gag-specific cytotoxic T lymphocytes defined with recombinant vaccine virus and synthetic peptides" *Nature*, Dec. 1988, pp. 484-487, vol. 336.

Tijhaar at at "*Salmonella typhimurium* aroA recombinants and immune-stimulating complexes as vaccine candidates for feline immunodeficiency virus" *J. General Virology*, 1997, 78:3265-3275.

Sjolander at al. "Induction of homologous virus neutralizing antibodies in guinea-pigs immunized with two human immunodeficiency virus type 1 glycoprotein gp120-iscom preparations" *Vaccine*, 1996, 14(4):344-352.

SCORE Sequence result No. 15.

Dunham "Lessons from the cat: development of vaccines against lentiviruses" *Veterinary Immunology and Immunopathology*, 2006, 112.

Elyar et al. "Perspectives on FIV vaccine development" *Vaccine*, 1997, 15(12/13):1437-1444.

Li, Y et al. "Complete Nucleotide Sequence, Genome Organization, and Biological Properties of Human Immunodeficiency Virus Type I In Vivo: Evidence for Limited Defectiveness and Complementation" *Journal of Virology*, 1992, 66(11):6587-6600.

\* cited by examiner

SEQUENCE LISTING

<160> NUMBER OF SEQ ID NOS: 8

<210> SEQ ID NO 1
<211> LENGTH: 848
<212> TYPE: PRT
<213> ORGANISM: Human immunodeficiency virus type 1

<400> SEQUENCE: 1

```
Met Arg Val Lys Gly Ile Arg Lys Ser Phe Gln Tyr Leu Trp Arg Trp
1               5                   10                  15

Gly Ile Met Leu Leu Gly Met Leu Met Ile Cys Ser Ala Thr Glu Lys
            20                  25                  30

Leu Trp Val Thr Val Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Ser Pro
65                  70                  75                  80

Gln Glu Val Glu Leu Gln Asn Val Thr Glu Asp Phe Asn Met Trp Lys
                85                  90                  95

Asn Asn Met Val Glu Gln Met His Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Lys Asn Ala Thr Asn Thr Ser Ser Ser Gly
    130                 135                 140

Gly Gly Thr Met Glu Arg Gly Glu Ile Lys Asn Cys Ser Phe Lys Ile
145                 150                 155                 160

Thr Thr Asn Ile Arg Asn Lys Met Gln Lys Glu Tyr Ala Leu Phe Asp
                165                 170                 175

Lys His Asp Val Val Pro Ile Asp Lys Lys Asn Thr Arg Tyr Arg Leu
            180                 185                 190

Ile Ser Cys Asn Thr Ser Val Ile Thr Gln Ala Cys Pro Lys Val Ser
        195                 200                 205
```

-continued

Phe Glu Pro Ile Pro Ile His Phe Cys Ala Pro Ala Gly Phe Ala Ile
210                 215                 220

Leu Lys Cys Lys Asp Lys Phe Asn Gly Lys Gly Ser Cys Thr Lys
225                 230                 235                 240

Val Ser Thr Val Gln Cys Thr His Gly Ile Arg Pro Val Val Ser Thr
                245                 250                 255

Gln Leu Leu Asn Gly Ser Leu Ala Glu Glu Val Val Ile Arg
                260                 265                 270

Ser Asp Asn Phe Thr Asp Asn Ala Lys Thr Ile Ile Val Gln Leu Asn
            275                 280                 285

Glu Thr Val Glu Ile Asn Cys Thr Arg Pro Asn Asn Thr Arg Lys
290                 295                 300

Arg Ile Thr Met Gly Pro Gly Arg Val Phe Tyr Thr Thr Gly Glu Ile
305                 310                 315                 320

Ile Gly Asp Ile Arg Arg Ala His Cys Asn Ile Ser Gly Thr Lys Trp
                325                 330                 335

Asn Asn Thr Leu Lys Gln Ile Val Thr Lys Leu Arg Glu Lys Phe Gly
                340                 345                 350

Asn Lys Thr Ile Val Phe Lys Gln Ser Ser Gly Gly Asp Pro Glu Ile
            355                 360                 365

Val Met His Thr Phe Asn Cys Gly Gly Glu Phe Phe Tyr Cys Asn Thr
370                 375                 380

Lys Gln Leu Phe Asn Ser Thr Trp Asn Asp Thr Asp Thr Leu Asn Asn
385                 390                 395                 400

Thr Glu Arg Ser Ser Lys Thr Ile Thr Leu Pro Cys Arg Ile Lys Gln
                405                 410                 415

Ile Ile Asn Met Trp Gln Glu Val Gly Lys Ala Met Tyr Ala Pro Pro
                420                 425                 430

Ile Ser Gly Gln Ile Arg Cys Ser Ser Asn Ile Thr Gly Leu Leu Leu
                435                 440                 445

Val Arg Asp Gly Gly Asn Asn Ala Glu Asn Glu Thr Glu Ile Leu Arg
            450                 455                 460

Pro Gly Gly Gly Asn Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
                485                 490                 495

Lys Arg Arg Val Val Gln Arg Glu Lys Arg Ala Val Gly Thr Leu Gly
                500                 505                 510

Ala Leu Phe Leu Gly Phe Leu Gly Thr Ala Gly Ser Thr Met Gly Ala
                515                 520                 525

Ala Ser Met Ala Leu Thr Val Gln Ala Arg Gln Leu Leu Ser Gly Ile
            530                 535                 540

Val Gln Gln Gln Asn Asn Leu Leu Arg Ala Ile Glu Ala Gln His
545                 550                 555                 560

Leu Leu Gln Leu Thr Val Trp Gly Ile Lys Gln Leu Gln Ala Arg Val
                565                 570                 575

Leu Ala Val Glu Arg Tyr Leu Lys Asp Gln Gln Leu Leu Gly Ile Trp
                580                 585                 590

Gly Cys Ser Gly Lys Phe Ile Cys Thr Thr Ala Val Pro Trp Asn Ala
            595                 600                 605

Ser Trp Ser Asn Lys Ser Leu Asp Lys Ile Trp Asn Asn Met Thr Trp
            610                 615                 620

Met Gln Trp Glu Arg Glu Ile Asp Asn Tyr Thr Asp Leu Ile Tyr Thr
625                 630                 635                 640

```
Leu Ile Glu Glu Ser Gln Asn Gln Gln Glu Lys Asn Glu Gln Glu Leu
                645                 650                 655

Leu Glu Leu Asp Lys Trp Ala Ser Leu Trp Asn Trp Phe Asp Ile Thr
            660                 665                 670

Lys Trp Leu Trp Tyr Ile Lys Ile Phe Ile Met Ile Val Gly Gly Leu
                675                 680                 685

Val Gly Leu Arg Ile Val Phe Ala Val Val Ser Ile Val Asn Arg Val
            690                 695                 700

Arg Gln Gly Tyr Ser Pro Leu Ser Phe Gln Thr His Phe Pro Ala Pro
705                 710                 715                 720

Arg Gly Pro Asp Arg Pro Glu Gly Ile Glu Glu Gly Gly Asp Arg
                725                 730                 735

Asp Arg Asp Arg Ser Ile Arg Leu Val Asp Gly Phe Leu Ala Leu Phe
            740                 745                 750

Trp Asp Asp Leu Arg Ser Leu Cys Leu Ser Ser Tyr His Arg Leu Arg
                755                 760                 765

Asp Leu Leu Leu Ile Val Thr Arg Ile Val Glu Leu Leu Gly Arg Arg
            770                 775                 780

Gly Trp Glu Ala Leu Lys Tyr Trp Trp Asn Leu Leu Gln Tyr Trp Ser
785                 790                 795                 800

Gln Glu Leu Lys Asn Ser Ala Ile Ser Leu Leu Asn Thr Thr Ala Ile
                805                 810                 815

Ala Val Ala Glu Gly Thr Asp Arg Val Ile Glu Ile Val Gln Arg Ala
            820                 825                 830

Tyr Arg Ala Val Ile His Ile Pro Arg Arg Ile Arg Gln Gly Phe Glu
                835                 840                 845

<210> SEQ ID NO 2
<211> LENGTH: 499
<212> TYPE: PRT
<213> ORGANISM: Human immunodeficiency virus type 1

<400> SEQUENCE: 2

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Asp Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Glu Asn Ile Glu Glu Glu Gln Asn Lys Ser Lys
                100                 105                 110

Lys Lys Ala Gln Pro Ala Asp Asp Thr Gly Asn Ser Ser Gln Val Ser
            115                 120                 125

Gln Asn Tyr Pro Val Val Gln Asn Leu Gln Gly Gln Met Val His Gln
        130                 135                 140

Pro Ile Ser Pro Arg Thr Leu Asn Ala Trp Val Lys Val Val Glu Glu
145                 150                 155                 160

Lys Ala Phe Ser Pro Glu Val Ile Pro Met Phe Thr Ala Leu Ser Glu
                165                 170                 175
```

Gly Ala Thr Pro Gln Asp Leu Asn Thr Met Leu Asn Thr Val Gly Gly
                    180                 185                 190

His Gln Ala Ala Met Gln Met Leu Lys Glu Thr Ile Asn Glu Glu Ala
            195                 200                 205

Ala Glu Trp Asp Arg Leu His Pro Val His Ala Gly Pro Ile Ala Pro
210                 215                 220

Asp Gln Met Arg Glu Pro Arg Gly Ser Asp Ile Ala Gly Ile Thr Ser
225                 230                 235                 240

Thr Leu Gln Glu Gln Ile Gly Trp Met Thr Asn Asn Pro Pro Ile Pro
                245                 250                 255

Val Gly Glu Ile Tyr Lys Arg Trp Ile Ile Leu Gly Leu Asn Lys Ile
            260                 265                 270

Val Arg Met Tyr Ser Pro Thr Ser Ile Leu Asp Ile Arg Gln Gly Pro
        275                 280                 285

Lys Glu Pro Phe Arg Asp Tyr Val Asp Arg Phe Tyr Lys Thr Leu Arg
    290                 295                 300

Ala Glu Gln Ala Ser Gln Asp Val Lys Asn Trp Met Thr Glu Thr Leu
305                 310                 315                 320

Leu Val Gln Asn Ala Asn Pro Asp Cys Lys Thr Ile Leu Lys Ala Leu
                325                 330                 335

Gly Pro Ala Ala Thr Leu Glu Glu Met Met Thr Ala Cys Gln Gly Val
            340                 345                 350

Gly Gly Pro Gly His Lys Ala Arg Val Leu Ala Glu Ala Met Ser Gln
        355                 360                 365

Val Thr Asn Ser Ala Thr Ile Met Met Gln Arg Gly Asn Phe Arg Asn
    370                 375                 380

Gln Arg Lys Ile Val Lys Cys Phe Asn Cys Gly Lys Glu Gly His Ile
385                 390                 395                 400

Thr Lys Asn Cys Arg Ala Pro Arg Lys Lys Gly Cys Trp Lys Cys Gly
                405                 410                 415

Lys Glu Gly His Gln Met Lys Asp Cys Thr Glu Arg Gln Ala Asn Phe
            420                 425                 430

Leu Gly Lys Ile Trp Pro Ser Lys Gly Arg Pro Gly Asn Phe Leu
        435                 440                 445

Gln Ser Arg Pro Glu Pro Thr Ala Pro Ala Glu Ser Phe Arg Phe
    450                 455                 460

Gly Glu Glu Thr Thr Thr Pro Ser Gln Lys Gln Glu Pro Thr Asp Lys
465                 470                 475                 480

Glu Leu Tyr Pro Leu Ala Ser Leu Arg Ser Leu Phe Gly Asn Asp Pro
                485                 490                 495

Ser Ser Gln

<210> SEQ ID NO 3
<211> LENGTH: 2545
<212> TYPE: DNA
<213> ORGANISM: Human immunodeficiency virus type 1

<400> SEQUENCE: 3
atgagagtga aggggatcag gaagagcttt cagtacttgt ggagatgggg catcatgctc    60
cttgggatgt tgatgatctg tagtgctaca gaaaaattgt gggtcacagt ctattatggg   120
gtacctgtgt ggaaagaagc aaccaccact ctatttgtg catcagatgc taaagcatat   180
gatacagagg tacataatgt ttgggccaca catgcctgtg tacccacaga ccccagccca   240
caagaagtag aattgcaaaa tgtgacagaa gattttaaca tgtggaaaaa taacatggta   300

```
gaacagatgc atgaggatgt aatcagtcta tgggatcaaa gcctaaagcc atgtgtaaaa    360
ttaaccccac tctgtgtcac tttaaattgc actgatttaa agaatgctac taataccact    420
agtagtagtg ggggaggaac gatggagaga ggagaaataa aaaactgctc tttcaaaatc    480
accacaaaca taagaaataa gatgcagaaa gaatatgcac ttttttgataa acatgatgta    540 gtaccaatag ataaaaagaa tactagatat aggttgataa gttgtaacac ctcagtcatt    600
acacaggcct gtccaaaggt atcctttgag ccaattccca tacatttttg tgccccggcc    660
ggttttgcga ttctaaagtg taaggataag aagttcaatg gaaagggatc atgtacaaaa    720
gtcagcacag tacaatgtac gcatggaatt aggccagtag tatcaactca actgctgtta    780
aatggcagtc tagcagaaga agaggtagta attagatctg acaatttcac agacaatgct    840
aaaaccataa tagtacagct gaatgaaact gtagaaatta attgtacaag acccaacaac    900
aatacaagga aacgtataac tatgggacca gggagagtat tttatacaac aggagaaata    960
ataggagata taagacgagc acattgtaac attagtggaa caaaatggaa taacacttta   1020
aaacagatag ttacaaaatt aagagaaaaa tttggaaata aaacaatagt ctttaagcaa   1080
tcctcaggag gggacccaga aattgtaatg cacactttta attgtggagg ggaattttc    1140 tactgtaaca caaacaact gtttaatagt acttggaatg atactgatac tctgaataat    1200
actgaaaggt caagtaaaac catcacgctc ccatgcagaa taaaacaaat tataaacatg   1260
tggcaggaag taggaaaagc aatgtatgcc cctcccatca gcggacaaat tagatgttca   1320
tcaaatatta cagggcttct attagtaaga gatggtggta ataatgctga gaacgagacc   1380
gagatcctca gacctggagg aggaaacatg agggacaatt ggagaagtga attatataaa   1440
tataaagtag taaaaattga accattagga gtagcaccca ccaaggcaaa gagaagagtg   1500
gtgcagagag aaaaaagagc agtgggaacg ctaggagctt tgttccttgg gttcttggga   1560
acagcaggaa gcactatggg cgcagcgtca atggcgctga cggtacaggc cagacaatta   1620
ttgtctggta tagtgcaaca gcagaacaat ttgctgaggg ctattgaggc gcaacagcat   1680
ttgttgcaac tcacagtctg ggcatcaag cagctccagg caagagtcct ggctgtggaa   1740
agatacctaa aggatcaaca gctcctaggg atttggggtt gctcgggaaa attcatttgc   1800
accactgctg tgccttggaa tgctagttgg agtaataaat ctctggataa gatttggaat   1860
aacatgacct ggatgcagtg ggaaagagaa attgacaatt acacagacct aatatacacc   1920
ttaattgaag aatcgcaaaa ccaacaagaa aagaatgaac aagaattatt ggaattagat   1980
aagtgggcaa gtttgtggaa ttggtttgac ataacaaaat ggctgtggta tataaaaata   2040
ttcataatga tagtaggagg cttggtaggt ttaagaatag ttttgctgt agtttctata   2100 gtgaatagag ttaggcaggg atactcacca ttatcatttc agacccactt cccagccccg   2160
aggggacccg acaggcccga aggaatcgaa gaagaaggtg gagacagaga cagagacaga   2220
tccattcgct tagtggatgg attcttagca ctcttctggg acgacctacg gagcctgtgc   2280
ctctccagct accaccgctt gagagactta ctcttgattg taacgaggat tgtggaactt   2340
ctgggacgca gggggtggga agccctcaaa tattggtgga atctcctgca gtattggagt   2400
caggaactaa agaatagtgc tattagcttg ctcaatacca cagctatagc agtagctgag   2460
gggacagata gggttataga aatagtacaa agagcttata gagctgttat ccacatacct   2520
agaagaataa gacagggctt tgaaa                                        2545
```

<210> SEQ ID NO 4
<211> LENGTH: 1605

```
<212> TYPE: DNA
<213> ORGANISM: Human immunodeficiency virus type 1

<400> SEQUENCE: 4
atgggtgcga gagcgtcagt attaagcggg ggagaattag ataaatggga aaaaattcgg     60
ttaaggccag ggggaaagaa aaatataaa ttaaaacata tagtatgggc aagcagggag    120
ctagaacgat tcgcagttaa tcctggcctg ttagaaacat cagacggctg tagacaaata    180
ctgggacagc tacaaccatc ccttcagaca ggatcagaag aacttagatc attatataat    240
acagtagcaa ccctctattg tgtgcatcaa aggatagagg taaaagacac caaggaagct    300
ttagagaata tagaggagga gcaaaacaaa agcaagaaaa agcacagcc agcagatgac     360
acaggaaaca gcagccaagt cagccaaaat taccctgtag tgcagaacct ccaggggcaa    420
atggtacatc agcccatatc acctagaact ttaaatgcat gggtaaaggt agtagaagag    480
aaggctttca gcccagaagt aatacccatg tttacagcat tatcagaagg agccacccca    540
caagatttaa acaccatgct aaacacagtg gggggacatc aagcagccat gcaaatgtta    600
aaagagacca tcaatgagga agctgcagaa tgggatagat tgcatccagt gcatgcaggg    660
cctattgcac cagaccagat gagagaacca aggggaagtg acatagcagg aattactagt    720
acccttcagg aacaaatagg atggatgaca ataatccac ctatcccagt aggagaaatc     780
tataaaagat ggataatcct gggattaaat aaaatagtaa gaatgtatag ccctaccagc    840
attctggaca agacaagg accaaggaa cccttagag actatgtaga ccggttctat        900
aaaactctaa gagccgagca gcttcacag gatgtaaaa attggatgac agaaaccttg      960
ttggtccaaa atgcaaaccc agattgtaag actattttaa aagcattggg accagcagct   1020
acactagaag aaatgatgac agcatgtcag ggagtggggg gacccggaca taaagcaaga   1080
gttttggctg aagcaatgag ccaagtaaca aattccgcca ccataatgat gcaaagaggc   1140
aattttagga accaaagaaa gattgttaag tgtttcaatt gtggcaaaga agggcacata   1200
accaaaaatt gcagggcccc taggaaaaag ggctgttgga atgtggaaa ggaaggacac    1260
caaatgaaag attgtactga gagacaggct aattttttag gaagatctg gccttccaag    1320
aaggggaggc cagggaattt tcttcagagc agaccagagc caacagcccc accagcagag   1380
agcttcaggt ttggggagga cacaacaact ccctctcaga gcaggagcc acagacaag    1440
gaactgtatc ccttagcttc cctcagatca ctctttggca acgacccctc gtcacaataa   1500
aggtaggggg gcaactaaag gaagctctat tagatacagg agcagatgat aagggcgaat   1560
tccagcacac tggcggccgt tactagtgga tccgagctcg gtacc                   1605

<210> SEQ ID NO 5
<211> LENGTH: 856
<212> TYPE: PRT
<213> ORGANISM: Human immunodeficiency virus type 1

<400> SEQUENCE: 5

Met Arg Val Lys Glu Lys Tyr Gln His Leu Arg Arg Trp Gly Trp Arg
 1               5                  10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
```

-continued

```
                65                  70                  75                  80
        Pro Gln Glu Val Val Leu Val Asn Val Thr Glu Asn Phe Asn Met Trp
                                85                  90                  95

Lys Asn Asp Met Val Glu Gln Met His Glu Asp Ile Ile Ser Leu Trp
                           100                 105                 110

Asp Gln Ser Leu Lys Pro Cys Val Lys Leu Thr Pro Leu Cys Val Ser
                           115                 120                 125

Leu Lys Cys Thr Asp Leu Lys Asn Asp Thr Asn Thr Asn Ser Ser Ser
                      130                 135                 140

Gly Gly Met Ile Met Glu Lys Gly Glu Ile Lys Asn Cys Ser Phe Asn
        145                 150                 155                 160

Ile Ser Thr Ser Ile Arg Gly Lys Val Gln Lys Glu Tyr Ala Phe Phe
                                165                 170                 175

Tyr Lys His Asp Ile Ile Pro Ile Asp Asn Asp Thr Thr Ser Tyr Thr
                           180                 185                 190

Leu Thr Ser Cys Asn Thr Ser Val Ile Thr Gln Ala Cys Pro Lys Val
                      195                 200                 205

Ser Phe Glu Pro Ile Pro Ile His Tyr Cys Ala Pro Ala Gly Phe Ala
                 210                 215                 220

Ile Leu Lys Cys Asn Asn Lys Thr Phe Asn Gly Thr Gly Pro Cys Thr
        225                 230                 235                 240

Asn Val Ser Thr Val Gln Cys Thr His Gly Ile Lys Pro Val Val Ser
                                245                 250                 255

Thr Gln Leu Leu Leu Asn Gly Ser Leu Ala Glu Glu Val Val Ile
                           260                 265                 270

Arg Ser Ala Asn Leu Thr Asp Asn Val Lys Thr Ile Ile Val Gln Leu
                      275                 280                 285

Asn Gln Ser Val Glu Ile Asn Cys Thr Arg Pro Asn Asn Asn Thr Arg
                 290                 295                 300

Lys Arg Ile Arg Ile Gln Arg Gly Pro Gly Arg Thr Phe Val Thr Ile
        305                 310                 315                 320

Gly Lys Ile Gly Asn Met Arg Gln Ala His Cys Asn Ile Ser Arg Ala
                                325                 330                 335

Lys Trp Asn Asn Thr Leu Lys Gln Ile Ala Ser Lys Leu Arg Glu Gln
                           340                 345                 350

Tyr Gly Asn Asn Lys Thr Ile Ile Phe Lys Gln Ser Ser Gly Gly Asp
                      355                 360                 365

Leu Glu Ile Val Thr His Ser Phe Asn Cys Gly Gly Glu Phe Phe Tyr
                 370                 375                 380

Cys Asn Ser Thr Gln Leu Phe Asn Ser Thr Trp Phe Asn Ser Thr Trp
        385                 390                 395                 400

Ser Thr Glu Gly Ser Asn Asn Thr Glu Gly Ser Asp Thr Ile Thr Leu
                                405                 410                 415

Pro Cys Arg Ile Lys Gln Ile Ile Asn Met Trp Gln Glu Val Gly Lys
                           420                 425                 430

Ala Met Tyr Ala Pro Pro Ile Ser Gly Gln Ile Arg Cys Ser Ser Asn
                      435                 440                 445

Ile Thr Gly Leu Leu Leu Thr Arg Asp Gly Gly Asn Asn Asn Asn Gly
                 450                 455                 460

Ser Glu Ile Phe Arg Pro Gly Gly Gly Asp Met Arg Asp Asn Trp Arg
        465                 470                 475                 480

Ser Glu Leu Tyr Lys Tyr Lys Val Val Lys Ile Glu Pro Leu Gly Val
                                485                 490                 495
```

```
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Ile Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly His Ser Pro Leu Ser Phe Gln Thr His
705                 710                 715                 720
Leu Pro Thr Pro Gly Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
            740                 745                 750
Leu Ala Leu Ile Trp Asp Asp Leu Arg Ser Leu Cys Leu Phe Ser Tyr
        755                 760                 765
His Arg Leu Arg Asp Leu Leu Leu Ile Val Thr Arg Ile Val Glu Leu
    770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
            820                 825                 830
Val Gln Gly Ala Cys Arg Ala Ile Arg His Ile Pro Arg Arg Ile Arg
        835                 840                 845
Gln Gly Leu Glu Arg Ile Leu Leu
    850                 855

<210> SEQ ID NO 6
<211> LENGTH: 500
<212> TYPE: PRT
<213> ORGANISM: Human immunodeficiency virus type 1

<400> SEQUENCE: 6

Met Gly Ala Arg Ala Ser Val Leu Ser Gly Gly Lys Leu Asp Arg Trp
1               5                   10                  15
```

-continued

```
Glu Lys Ile Arg Leu Arg Pro Gly Gly Lys Lys Tyr Lys Leu Lys
         20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Arg Gln Ile Leu Gly Gln Leu
 50                  55                  60

Gln Pro Ser Leu Gln Thr Gly Ser Glu Glu Cys Arg Ser Leu Tyr Asn
 65                  70                  75                  80

Thr Val Ala Thr Leu Tyr Cys Val His Gln Arg Ile Glu Ile Lys Asp
             85                  90                  95

Thr Lys Glu Ala Leu Asp Lys Ile Lys Glu Glu Gln Asn Lys Ser Lys
         100                 105                 110

Lys Lys Ala Gln Gln Ala Ala Ala Asp Thr Gly His Ser Ser Gln Val
         115                 120                 125

Ser Gln Asn Tyr Pro Ile Val Gln Asn Ile Gln Gly Gln Met Val His
         130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                 165                 170                 175

Glu Gly Ala Thr Pro Gln Asp Leu Asn Thr Met Leu Asn Thr Val Gly
             180                 185                 190

Gly His Gln Ala Ala Met Gln Met Leu Lys Glu Thr Ile Asn Glu Glu
         195                 200                 205

Ala Ala Glu Trp Asp Arg Val His Pro Val His Ala Gly Pro Ile Ala
         210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                 245                 250                 255

Pro Val Gly Glu Ile Tyr Lys Arg Trp Ile Ile Leu Gly Leu Asn Lys
             260                 265                 270

Ile Val Arg Met Tyr Ser Pro Thr Ser Ile Leu Asp Ile Arg Gln Gly
         275                 280                 285

Pro Lys Glu Pro Phe Arg Asp Tyr Val Asp Arg Phe Tyr Lys Thr Leu
         290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                 325                 330                 335

Leu Gly Pro Ala Ala Thr Leu Glu Glu Met Met Thr Ala Cys Gln Gly
             340                 345                 350

Val Gly Gly Pro Gly His Lys Ala Arg Val Leu Ala Glu Ala Met Ser
         355                 360                 365

Gln Val Thr Asn Ser Ala Thr Ile Met Met Gln Arg Gly Asn Phe Arg
         370                 375                 380

Asn Gln Arg Lys Ile Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
                 405                 410                 415

Gly Lys Glu Gly His Gln Met Lys Asp Cys Thr Glu Arg Gln Ala Asn
             420                 425                 430

Phe Leu Gly Lys Ile Trp Pro Ser Tyr Lys Gly Arg Pro Gly Asn Phe
         435                 440                 445
```

| | | | | | | | | | | | |
|---|---|---|---|---|---|---|---|---|---|---|---|
|Leu|Gln|Ser|Arg|Pro|Glu|Pro|Thr|Ala|Pro|Pro|Glu Glu Ser Phe Arg|
| |450| | | |455| | | |460| | |

Ser Gly Val Glu Thr Thr Thr Pro Pro Gln Lys Gln Glu Pro Ile Asp
465             470             475             480

Lys Glu Leu Tyr Pro Leu Thr Ser Leu Arg Ser Leu Phe Gly Asn Asp
                485             490             495

Pro Ser Ser Gln
            500

<210> SEQ ID NO 7
<211> LENGTH: 2571
<212> TYPE: DNA
<213> ORGANISM: Human immunodeficiency virus type 1

<400> SEQUENCE: 7

```
atgagagtga aggagaaata tcagcacttg cggagatggg ggtggagatg gggcaccatg      60
ctccttggga tgttgatgat ttgtagtgct acagaaaaat tgtgggtcac agtctattat     120
ggggtacctg tgtggaagga agcaaccacc actctatttt gtgcatcaga tgctaaagca     180
tatgatacag aggtacataa tgtttgggcc acacatgcct gtgtacccac agaccccaac     240
ccacaagaag tagtattggt aaatgtgaca gaaaatttta acatgtggaa aaatgatatg     300
gtagaacaga tgcatgagga tataatcagt ttatgggatc aaagcctaaa gccatgtgta     360
aaattaaccc cactctgtgt tagtttaaag tgcactgatt tgaagaatga tactaatacc     420
aatagtagta gcgggggaat gataatgag aaaggagaga taaaaaactg ctctttcaat     480
atcagcacaa gcataagagg taaggtgcag aaagaatatg cattttttta taaacatgat     540
ataataccaa tagataatga tactaccagc tatacgttga caagttgtaa cacctcagtc     600
attacacagg cctgtccaaa ggtatccttt gagccaattc ccatacatta ttgtgccccg     660
gctggttttg cgattctaaa atgtaataat aagacgttca atggaacagg accatgtaca     720
aatgtcagca cagtacaatg tacacatgga attaagccag tagtatcaac tcaactgctg     780
ttaaatggca gtctagcaga agaaggta gtaattgat ctgccaatct cacagacaat     840
gttaaaacca atagtacaa gctgaaccaa tctgtagaaa ttaattgtac aagacccaac     900
aacaatacaa gaaaagaat ccgtatccag agaggaccag ggagaacatt tgttacaata     960
ggaaaaatag gaaatatgag acaagcacat tgtaacatta gtagagcaaa atggaataac    1020
actttaaaac agatagctag caaattaaga gaacaatatg gaataataa aacaataatc    1080
tttaagcagt cctcaggagg ggacctagaa attgtaacgc acagttttaa ttgtggaggg    1140
gaatttttct actgtaattc aacacaactg tttaatagta cttggtttaa tagtacttgg    1200
agtactgaag ggtcaaataa cactgaagga agtgacacaa tcacactccc atgcagaata    1260
aaacaaatta taaacatgtg gcaggaagta ggaaaagcaa tgtatgcccc tcccatcagc    1320
ggacaaatta gatgttcatc aaatattaca gggctgctat taacaagaga tggtggtaat    1380
aacaacaatg ggtccgagat cttcagacct ggaggaggag atatgaggga caattggaga    1440
agtgaattat ataaatataa agtagtaaaa attgaaccat taggagtagc acccaccaag    1500
gcaaagagaa gagtggtgca gagagaaaaa agagcagtgg gaataggagc tttgttcctt    1560
gggttcttgg gagcagcagg aagcactatg ggcgcagcgt caatgacgct gacggtacag    1620
gccagacaat tattgtctgg tatagtgcag cagcagaaca atttgctgag ggctattgag    1680
gcgcaacagc atctgttgca actcacagta tggggcatca agcagctcca ggcaagaatc    1740
ctggctgtgg aaagatacct aaaggatcaa cagctcctgg ggatttgggg ttgctctgga    1800
```

```
aaactcattt gcaccactgc tgtgccttgg aatgctagtt ggagtaataa atctctggaa    1860
cagatttgga atcacacgac ctggatggag tgggacagag aaattaacaa ttacacaagc    1920
ttaatacact ccttaattga agaatcgcaa aaccaacaag aaaagaatga acaagaatta    1980
ttggaattag ataaatgggc aagtttgtgg aattggttta acataacaaa ttggctgtgg    2040
tatataaaaa tattcataat gatagtagga ggcttggtag gtttaagaat agttttgct    2100 gtactttcta tagtgaatag agttaggcag ggacattcac cattatcgtt tcagacccac    2160
ctcccaaccc cggggggacc cgacaggccc gaaggaatag aagaagaagg tggagagaga    2220
gacagagaca gatccattcg attagtgaac ggatccttag cacttatctg ggacgatctg    2280
cgaagcctgt gcctcttcag ctaccaccgc ttgagagact tactcttgat tgtaacgagg    2340
attgtggaac ttctgggacg caggggggtgg gaagccctca aatattggtg gaatctccta    2400
cagtattgga gtcaggaact aaagaatagt gctgttagct tgctcaatgc cacagccata    2460
gcagtagctg aggggacaga tagggttata gaagtagtac aaggagcttg tagagctatt    2520
cgccacatac ctagaagaat aagacagggc ttggaaagga ttttgctata a             2571

<210> SEQ ID NO 8
<211> LENGTH: 1503
<212> TYPE: DNA
<213> ORGANISM: Human immunodeficiency virus type 1

<400> SEQUENCE: 8
atgggtgcga gagcgtcagt attaagcggg ggaaaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aatgtagatc attatataat     240
acagtagcaa ccctctattg tgtgcatcaa aggatagaga taaaagacac caaggaagct     300
ttagacaaga taaaggaaga gcaaaacaaa agtaagaaaa aagcacagca agcagcagct     360
gacacaggac acagcagtca ggtcagccaa aattacccta tagtgcagaa catccagggg     420
caaatggtac atcaggccat atcacctaga actttaaatg catgggtaaa agtagtagaa     480
gagaaggctt tcagcccaga agtaataccc atgttttcag cattatcaga aggagccacc     540
ccacaagatt taaacaccat gctaaacaca gtggggggac atcaagcagc catgcaaatg     600
ttaaaagaga ccatcaatga ggaagctgca gaatgggata gagtgcatcc agtgcatgca     660
gggcctatcg caccaggcca gatgagagaa ccaaggggaa gtgacatagc aggaactact     720
agtacccttc aggaacaaat aggatggatg acaaataatc cacctatccc agtaggagaa     780
atttataaaa gatggataat cctgggatta aataagatag taagaatgta tagccctacc     840
agcattctgg acataagaca aggaccaaaa gaaccttttta gagactatgt agaccggttc     900
tataaaactc taagagccga gcaagcttca caggaggtaa aaaattggat gacagaaacc     960
ttgttggtcc aaaatgcgaa cccagattgt aagactattt taaaagcatt gggaccagca    1020
gctacactag aagaaatgat gacagcatgt caggagtgtgg gaggacccgg ccataaggca    1080
agagttttgg ctgaagcaat gagccaagta acaaattcag ctaccataat gatgcagaga    1140
ggcaatttta ggaaccaaag aaagattgtt aagtgtttca attgtggcaa agaagggcac    1200
atagccagaa attgcagggc ccctaggaaa aagggctgtt ggaaatgtgg aaaggaagga    1260
caccaaatga aagattgtac tgagagacag gctaattttt tagggaagat ctggccttcc    1320
tacaagggaa ggccagggaa ttttcttcag agcagaccag agccaacagc cccaccagaa    1380
```

```
gagagcttca ggtctggggt agagacaaca actcccctc agaagcagga gccgatagac   1440
aaggaactgt atcctttaac ttccctcaga tcactctttg gcaacgaccc ctcgtcacaa  1500
taa                                                                1503
```

US 8,703,145 B2

MATERIALS AND METHODS FOR IMMUNIZING AGAINST FIV INFECTION

CROSS REFERENCE TO RELATED APPLICATIONS

This application is a continuation of U.S. application Ser. No. 10/844,658, filed May 12, 2004, now abandoned, which claims the benefit of U.S. Provisional Application Ser. No. 60/470,066, filed May 12, 2003, each of which is hereby incorporated by reference in its entirety, including all figures, nucleic acid sequences, amino acid sequences, and tables.

The subject invention was made with government support under a research project supported by National Institutes of Health Grant No. NIH AI30904. The government has certain rights in this invention.

BACKGROUND OF THE INVENTION

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4: CD8 cell ratio and, in some cases, an increase in CD8-bearing lymphocytes. Based on molecular, biochemical and immunopathologic characteristics, FIV infection of cats is now considered to be a better feline AIDS model than FeLV-FAIDS.

Cloning and sequence analysis of FIV has been reported in Olmsted et al. (1989a); Olmsted et al. (1989b); and Talbott et al. (1989). Hosie and Jarrett (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al., 1994; Rigby et al., 1993; and Louwagie et al., 1993), little is known about the correlation between the genotype and immunotype of subtypes. FIV viral isolates have been classified into four FIV subtypes: A, B, C and D. (Kakinuma et al., 1995). Infectious isolates and infectious molecular clones have been described for all FIV subtypes except for subtype C (Sodora et al., 1994). Subtype C FIV has only been identified from cellular DNA of cats from Canada (Sodora et al., 1994; Rigby et al., 1993; Kakinuma et al., 1995). FIV strains identified in the art include (subtype of the strain is shown in parenthesis) Petaluma (A), Dixon (A), UK8 (A), Dutch113 (A), Dutch19K (A), UK2 (A), SwissZ2 (A), Sendai-1 (A), USCAzepy01A (A), USCAhnky11A (A), USCAtt-10A (A), USCAlemy01 (A), USCAsam-01A (A), PPR (A), FranceWo, Netherlands, Bangston (A/B), Aomori-1 (B), Aomori-2 (B), USILbrny03B (B), TM2 (B), Sendai-2 (B), USCKlgri02B (B), Yokohama (B), USMAsboy03B (B), USTXmtex03B (B), USMCglwd03B (B), CABCpbar03C (C), CABCpbar07C (C), CABCpady02C (C), Shizuoka (D), and Fukuoka (D).

One concern with the use of FIV-derived immunogens in a vaccine is that veterinary practitioners may be unable to tell whether a cat that tests positive for antibodies to FIV or FIV proteins has been infected with FIV or if the antibodies resulted from the cat being vaccinated against FIV using FIV-derived immunogens. Thus, there remains a need in the art for a vaccine that protects against FIV infection but that allows the practitioner to determine whether antibodies to FIV are a result of infection or immunization of a cat.

BRIEF SUMMARY OF THE INVENTION

The subject invention pertains to methods and compositions for protecting feline animals from infection by FIV using immunogens derived from primate immunodeficiency viruses, including HIV and SIV. Methods and compositions for vaccinating feline animals with the subject vaccine compositions are described. Feline animals vaccinated according to the methods and compositions of the subject invention exhibit protective immune responses to FIV when challenged with FIV.

The subject invention also concerns methods for selecting for epitopes that are evolutionarily conserved among immunodeficiency viruses. Evolutionarily conserved epitopes of immunodeficiency viruses identified using methods of the present invention also constitute part of the invention. The subject invention further concerns methods for protecting humans and other animals against infection by immunodeficiency viruses, such as HIV and FIV.

BRIEF DESCRIPTION OF THE SEQUENCES

SEQ ID. NO: 1 is an amino acid sequence of an HIV-$1_{UCD1}$ envelope protein.

SEQ ID NO: 2 is an amino acid sequence of an HIV-$1_{UCD1}$ gag protein.

SEQ ID NO: 3 is a nucleotide sequence of an HIV-$1_{UCD1}$ polynucleotide encoding an envelope protein.

SEQ ID NO: 4 is a nucleotide sequence of an HIV-$1_{UCD1}$ polynucleotide encoding a gag protein.

SEQ ID. NO: 5 is an amino acid sequence of an HIV-$1_{IIIB}$ envelope protein.

SEQ ID NO: 6 is an amino acid sequence of an HIV-$1_{IIIB}$ gag protein.

SEQ ID NO: 7 is a nucleotide sequence of an HIV-$1_{IIIB}$ polynucleotide encoding an envelope protein.

SEQ ID NO: 8 is a nucleotide sequence of an HIV-$1_{IIIB}$ polynucleotide encoding a gag protein.

DETAILED DISCLOSURE OF THE INVENTION

The subject invention concerns materials and methods for protecting a feline animal from infection by FIV by administering to the animal immunogens derived from primate immunodeficiency viruses, such as human immunodeficiency virus (HIV) or simian immunodeficiency virus (SIV). In one embodiment, an effective amount of a composition comprising an immunogen or immunogens derived from a primate immunodeficiency virus is administered to a feline animal. In addition, the various immunogen compositions described herein can be used separately and in combination with each other.

Advantageously, the present invention allows for protection against FIV infection wherein the generation of an immune response against FIV in the animal allows a veterinarian or other person of ordinary skill in the art to determine whether an animal's immune response to FIV or FIV immunogens or antigens is a result of an immunization to protect against FIV infection or if it is a result of FIV infection in the animal. In one embodiment, animals immunized using a vaccine composition of the present invention do not produce antibodies that cross-react with FIV gp95. Animals that have been infected with FIV or that may have received vaccines containing FIV-derived immunogens or antigens produce antibodies that bind to FIV gp95. Feline animals encompassed within the scope of the present invention include domestic house cats, feral cats, and other wild cats including bobcat, cougar, mountain lion, tiger, jaguar, leopard, puma, cheetah, and lion.

The present invention can also be used to generate an immune response, cellular and/or humoral, against FIV in a feline animal using immunogens derived from primate immunodeficiency viruses, such as HIV and SIV. In one embodiment, an amount of an immunogen sufficient to induce an immune response against FIV is administered to a feline animal. Serum antibodies from immunized cats can be tested for virus neutralizing antibody activity against HIV using PBMCs from healthy HIV-uninfected humans as indicator cells. Lymphocytes from immunized cats can be tested for both HIV-specific T-helper (Th) and cytotoxic T lymphocyte (CTL) activities. Th and CTL activity can be measured by the level of Th cytokines and CTL cytotoxins produced by the lymphocytes from unimmunized and immunized cats in response to in vitro stimulation with inactivated HIV whole-virus that are either the same as (homologous) or different from (heterologous to) the immunogen strain(s). The inactivated heterologous strains used for the in vitro stimulation can be from the same or different subtypes as the immunogen strain(s). Preferred immunogens produce high levels of Th cytokines in the cultures with $CD4^+$ T lymphocytes from immunized cats and is indicative. Similarly, preferred immunogens produce high levels of CTL cytotoxin(s) by $CD8^+$ T lymphocytes from immunized cats.

Primate immunodeficiency viruses encompassed within the scope of the present invention include HIV and SIV. In regard to HIV, the virus can be from either HIV-1 or HIV-2. In one embodiment, the HIV is HIV-1. Several distinct strains of HIV-1 have been described in the art and include HIV-$1_{IIIB}$, HIV-$1_{UCD1}$, HIV-$1_{LAV}$, and HIV-$1_{BRU}$. In an exemplified embodiment described herein, immunogens of the present invention are derived from the strain of HIV-1 designated as HIV-$1_{IIIB}$ and/or HIV-$1_{UCD1}$. SIV strains included within the scope of the invention are $SIV_{syk}$, $SIV_{smm}$, $SIV_{mac}$, $SIV_{mnd}$, $SIV_{l'hoest}$, $SIV_{agm}$ and $SIV_{cpz}$ (Whetter et al. 1999). The nucleotide sequences of numerous HIV and SIV genes have been described in the scientific literature, deposited in sequence databanks, such as the NCBI Genbank, and have been disclosed in published patent applications and issued patents. For example, complete genome sequences of HIV-1 and HIV-2 isolates are disclosed at Genbank accession numbers NC 001802 and NC 001722. Similarly, amino acid sequences of proteins encoded by HIV and SIV genes have been disclosed and are well known in the art. Genes of primate immunodeficiency viruses that encode proteins include env, gag, pol, and nef.

Immunogens derived from primate immunodeficiency viruses can be in isolated form or provided in any suitable composition. Preferably, the primate immunodeficiency viral immunogens are provided in a composition and administered in a manner to induce a strong cell-mediated and humoral immune response to the immunogen in a feline animal. In one embodiment, immunogens can be provided in the form of virus infected cells or whole cell-free virus. Virus in virus-infected cells and cell-free virus can be treated in a manner to inactivate or attenuate the virus. Methods for inactivating or attenuating virus are known in the art, and include, for example, treatment with paraformaldehyde, formalin, phenol, UV light, elevated temperature and the like. U.S. Pat. No. 6,503,753 describes methods for photoinactivation of HIV reverse transcriptase which thereby inactivates the HIV virus. Primate immunodeficiency viruses can also be prepared that are replication-defective. U.S. Pat. No. 6,500,623 describes HIV replication-defective viral particles and means for producing them. Other techniques for producing inactivated, attenuated and replication defective viruses are known in the art.

In another embodiment, immunogens of the invention are derived from viral proteins, or immunogenic fragments or variants thereof, of primate immunodeficiency viruses. Proteins that can be utilized as immunogens in the present invention include, but are not limited to, proteins encoded by the env, gag, pol, tat, rev, and/or nef genes. In one embodiment, envelope proteins encoded by the env gene that can be used in the invention include the envelope proteins gp120 and gp160, including fragments thereof, fusions of gp120 and gp160, and variations of gp120 and gp160, including variations in glycosylation which includes gp120 and/or gp160 proteins that are unglycosylated. A cellular protein cleaves gp160 into gp41 and gp120 moieties. The gp41 moiety comprises the transmembrane domain of the envelope protein, whereas gp120 is located on the surface of the infected cell or virion. The gp120 molecule consists of a polypeptide core of approximately 60 kd, but N-linked glycosylation can increase the molecular weight of the protein to approximately 120 kd. The viral envelope proteins used in conjunction with the present invention can be either unclipped or clipped (see, for example, U.S. Pat. No. 5,849,533). Envelope protein variants have been described in U.S. Pat. No. 5,846,546. Synthetic peptides which immunologically mimic HIV gp120 and/or gp160 envelope proteins can also be used in the present invention (see, for example, U.S. Pat. No. 5,763,160). In an exemplified embodiment, a combination of gp120 and gp160 envelope protein from HIV-$1_{IIIB}$ is utilized as an immunogen. In one embodiment, the envelope polypeptide of HIV-$1_{UCD-1}$ comprises the amino acid sequence shown in SEQ ID NO: 1. In one embodiment, the envelope polypeptide of HIV-$1_{IIIB}$ comprises the amino acid sequence shown in SEQ ID NO: 5.

Proteins encoded by a primate immunodeficiency virus gag gene, such as the p17 matrix protein, the p24 capsid protein, and the p7 nucleocapsid protein of HIV and the p27 protein of SIV, and fragments and variants thereof, can also be used in accordance with the present invention. In an exemplified embodiment, a p24 protein from HIV-$1_{UCD-1}$ is utilized as an immunogen. In one embodiment, the p24 polypeptide of HIV-$1_{UCD-1}$ comprises amino acids 132 to 362 of SEQ ID NO: 2. In one embodiment, the p24 polypeptide of HIV-$1_{IIIB}$ comprises amino acids 132 to 363 of SEQ ID NO: 6. Immunological fragments of the p24 protein have been described in U.S. Pat. No. 5,700,469. Proteins encoded by a primate immunodeficiency virus pol gene, such as reverse transcriptase (RT) protease (PR), and Rnase H of HIV, and fragments and variants thereof, can also be used in the present invention. Endonuclease protein p31 of HIV, and fragments and variants thereof, which is a protein encoded at the 3'-end of the pol gene of HIV, can also be used in accordance with the present invention. Immunological peptide fragments of the p31 protein of HIV have been described in U.S. Pat. No. 5,401,628. Regulatory proteins encoded by tat and rev genes of primate immunodeficiency viruses, and accessory proteins encoded by nef, vif, vpr, vpu, and vpx genes of primate immunodeficiency viruses, and fragments and variants of these proteins, can also be used in the present invention.

Peptides corresponding to immunogenic or antigenic regions of primate immunodeficiency viruses can be synthesized or prepared by recombinant means and utilized in the methods of the present invention. In one embodiment, peptides that correspond to overlapping fragments of a primate immunodeficiency virus protein can be prepared and used in the methods of the present invention. Any suitable combination of the peptide fragments can be used for immunizing an animal according to methods of the present invention. For example, peptide fragments that correspond to the carboxy terminus region of a viral protein can be used with peptide fragments that correspond to an amino terminus region or a transmembrane region of the protein.

Recombinant virus or viral vector-based expression constructs that comprise, primate immunodeficiency virus nucleotide sequences, for example, HIV or SIV env, gag, pol, tat, rev, nef, vif, vpu, vpr, gag/pol, or env-gag/pol sequences, or fragments or variants thereof, are also contemplated for use with the present invention. Any suitable viral vector that can be used to prepare recombinant vector/HIV or recombinant vector/SIV constructs is contemplated for use with the subject invention. For example, viral vectors derived from adenovirus, avipox, feline herpesvirus, vaccinia, canarypox, entomopox, swinepox and others known in the art can be used with the compositions and methods of the present invention. Recombinant polynucleotide vectors that encode and that can express HIV or SIV components in a suitable host cell can be constructed using standard genetic engineering techniques known in the art.

DNA or RNA vaccines which comprise nucleic acid that encodes one or more primate immunodeficiency virus proteins, or a fragment or variant thereof, are also contemplated for use in the subject invention. The nucleic acid can be provided in the form of a plasmid or eukaryotic expression construct. DNA vaccines and formulations have been described, for example, in published patent applications 20040076632; 20040047878; 20040009941; 20020156037; 20020032165; and 20010004531.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lek promoter, BMP5 promoter, TRP-1 promoter, murine mammary tumor virus long terminal repeat promoter, STAT promoter, or an immunoglobulin promoter can be used in the expression construct.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the immunogens of the invention. Chemical enhancers are cis-acting elements that increase gene transcription and can also be included in the expression construct. Chemical enhancer elements are known in the art, and include, but are not limited to, the cytomegalovirus (CMV) early promoter enhancer element and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the invention can also be introduced in vivo via lipofection (DNA transfection via liposomes prepared from synthetic cationic lipids) (Feigner et al., 1987). Synthetic cationic lipids (LIPO-FECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced as naked DNA using methods known in the art, such as transfection, microinjection, electroporation, calcium phosphate precipitation, and by biolistic methods.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the exemplified sequences. The polynucleotide includes both the sense and antisense strands as either individual strands or in the duplex.

The methods of the present invention contemplate a primary immunization with a vaccine composition of the invention. Subsequent or secondary immunizations are also contemplated within the scope of the subject methods. The vaccine composition used for secondary immunizations can be the same as or vary from the composition used for primary immunization. For example, primary immunizations of an animal may use recombinant vector-based HIV or SIV constructs, having single or multiple strain components, followed by secondary boosts with vaccine compositions comprising HIV- or SIV-infected cell lines, or HIV or SIV polypeptides, or cell free HIV or SIV virus, also having single or multiple strain components. Primary immunizations can also use an HIV and/or SIV DNA vaccine. In one embodiment, a recombinant vector construct is used for the primary immunization, whereas a protein, or protein plus recombinant vector construct, subunit vaccine composition is used for secondary boosts. In addition, the subject invention contemplates methods wherein the immunogen(s) used for a primary immunization is an HIV or SIV derived immunogen, e.g., an HIV p24 protein, and the immunogen(s) used for secondary immunizations are derived from FIV, e.g., FIV gp95 and/or gp36 protein, or whole FIV virus, or FIV-infected cells. Other immunization protocols with the vaccine compositions of the invention are apparent to persons skilled in the art and are contemplated within the scope of the present invention.

In one embodiment, immunogens from various primate immunodeficiency viral proteins are combined for administration to an animal. In an exemplified embodiment, a composition comprising an immunogen of HIV-1 p24 and an immunogen of HIV-1 gp120 and gp160 is administered to a feline animal. In another exemplified embodiment, a composition comprising HIV-1 p24 as the only immunogen is administered to a feline animal.

The subject invention also concerns materials and methods for protecting a feline animal against infection by an FIV or for generating an immune response against an FIV by administering to the animal a composition comprising immunogens derived from primate immunodeficiency viruses and immunogens derived from FIV. FIV-derived immunogens have been described in the art. See, for example, U.S. Pat. Nos. 5,118,602; 5,565,319; 5,510,106; 5,275,813; 5,037,753; and 4,861,720. FIV immunogens that can be used in accordance with the subject invention can be either of a single subtype or strain of FIV, or the immunogen can be derived from multiple subtypes of FIV. Multi-subtype FIV immunogens have been described in U.S. Pat. Nos. 5,846,825; 6,254,872; and 6,447,993.

In one embodiment of the subject methods, the immunogen to be administered to a feline animal comprises an epitope that is conserved between the primate immunodeficiency virus and FIV. In a further embodiment, the conserved epitope is present in the envelope protein of an immunodeficiency virus. Also contemplated within the scope of the invention are molecules (mimotope) which have a conformation that has a topology equivalent to a conserved epitope of the present invention and which binds to the same antigen-binding region of an antibody that binds to the conserved epitope. Typically, mimotopes are peptide molecules, but mimotopes can also be prepared from other non-peptide molecules.

The subject invention also concerns immunogens derived from a primate immunodeficiency virus, wherein the immunogen is a protein or peptide and comprises an epitope conserved between the primate immunodeficiency virus and FIV. In an exemplified embodiment, the immunogen comprises a gp120 and gp160 protein from HIV-1$_{IIIB}$, and, optionally, a p24 protein from HIV$_{UCD1}$. In another embodiment, the immunogen comprises a p24 protein from HIV$_{UCD1}$. The subject invention also concerns polynucleotides that encode the protein or peptides comprising conserved epitopes of the immunodeficiency virus derived immunogens.

The subject invention also concerns antibodies that cross-react with epitopes of the immunogens derived from primate immunodeficiency viruses and FIV. The antibodies can be polyclonal or monoclonal in form. The antibodies can be derived from any animal capable of producing antibodies to the epitopes, and include, for example, human, ape, monkey, mouse, rat, goat, sheep, pig, cow, and feline animals. Also contemplated within the scope of the invention are non-human antibodies that cross-react with an epitope of the immunogen derived from a primate immunodeficiency virus and FIV but that have been "humanized" using standard procedures known in the art, such as those described in U.S. Pat. Nos. 5,530,101; 5,585,089; 5,693,762; 6,180,370; and 6,407,213.

Peptide and/or polypeptide immunogens of the present invention can also be provided in the form of a multiple antigenic peptide (MAP) construct. The preparation of MAP constructs has been described in Tam (1988). MAP constructs utilize a core matrix of lysine residues onto which multiple copies of an immunogen are synthesized (Posnett et al., 1988). Multiple MAP constructs, each containing the same or different immunogens, can be prepared and administered in a vaccine composition in accordance with methods of the present invention. in one embodiment, a MAP construct is provided with and/or administered with one or more adjuvants.

Natural, recombinant or synthetic polypeptides of primate immunodeficiency viral proteins, and peptide fragments thereof, can also be used as vaccine compositions according to the subject methods. In one embodiment, different polypeptides are administered as a combined preparation to a feline animal. In an exemplified embodiment, HIV-1 gp120/160 and HIV-1 p24 polypeptides are administered to a feline animal. In another embodiment, HIV polypeptides derived from more than one HIV strain are combined in a vaccine composition and are used to vaccinate a host animal. For example, polypeptides based on the HIV envelope glycoprotein from at least two strains of HIV-1 can be combined in the vaccine. The polypeptides may comprise "hybrid" or "chimeric" polypeptides whose amino acid sequence is derived from joining or linking polypeptides from at least two distinct HIV strains. Procedures for preparing HIV polypeptides are well known in the art. For example, HIV polypeptides can be synthesized using solid-phase synthesis methods (Merrifield, 1963). HIV polypeptides can also be produced using recombinant DNA techniques wherein a polynucleotide molecule encoding an HIV protein or peptide is expressed in a host cell, such as bacteria, yeast, or mammalian cell lines, and the expressed protein purified using standard techniques of the art.

According to the methods of the subject invention, the immunogenic compositions described herein are administered to susceptible hosts, typically domestic cats, in an effective amount and manner to induce protective immunity against subsequent challenge or infection of the host by FIV. The immunogens are typically administered parenterally, by injection, for example, either subcutaneously, intraperitoneally, or intramuscularly, or by oral or nasal administration, or any combination of such routes of administration. Usually, the immunogens are administered to a host animal at least two times, with an interval of one or more weeks between each administration. However, other regimens for the initial and booster administrations of the immunogens are contemplated, and may depend on the judgment of the practitioner and the particular host animal being treated.

Immunogens that can be used in accordance with the present invention can be provided with a pharmaceutically-acceptable carrier or diluent. Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin, Easton Pa., Mack Publishing Company, 19$^{th}$ ed., 1995, describes formulations which can be used in connection with the subject invention. In general, the compositions of the subject invention will be formulated such that an effective amount of an immunogen is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of an immunogen of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the immunogen or immunogens based on the weight of the total composition including carrier or diluent.

The immunogenic compositions of the subject invention can be prepared by procedures well known in the art. For example, the immunogens are typically prepared as injectables, e.g., liquid solutions or suspensions. The immunogens are administered in a manner that is compatible with dosage formulation, and in such amount as will be therapeutically effective and immunogenic in the recipient. The optimal dosages and administration patterns for a particular immunogens formulation can be readily determined by a person skilled in the art.

As noted above, virus and cells in a immunogenic formulation may be inactivated or attenuated using methods known in the art. The amount of cell-free whole or partial virus in a vaccine dose will usually be in the range from about 0.1 mg to about 5 mg, and more usually being from about 0.2 mg to about 2 mg. The dosage for formulations comprising virus-infected cell lines will usually contain from about $10^6$ to about $10^8$ cells per dose, and more usually from about $5\times10^6$ to about $7.5\times10^7$ cells per dose. The amount of protein or peptide immunogen in a dose for a feline animal can vary from about 0.1 µg to 10000 µg, or about 1 µg to 5000 µg, or about 10 µg to 1000 µg, or about 25 µg to 750 µg, or about 50 µg to 500 µg, or 100 µg to 250 µg, depending upon the size, age, etc., of the animal receiving the dose.

In one embodiment, an immunogen of the invention is provided with one or more adjuvants that increase the animal's immune response against the immunogen. Immunogens of the invention can be provided with and/or administered with any suitable adjuvant or adjuvants known in the art. Adjuvants that can be used in the immunogen formulations of the invention include threonyl muramyl dipeptide (MDP) (Byars et al., 1987), Ribi adjuvant system components (Corixa Corp., Seattle, Wash.) including the cell wall skeleton (CWS) component, Freund's complete, and Freund's incomplete adjuvants or a combination thereof. A variety of other adjuvants suitable for use with the methods and vaccines of the subject invention, such as alum, aluminum hydroxide, and saponin are well known in the art and are contemplated for use with the subject invention. Cytokines ($\gamma$-IFN, GM-CSF, CSF, etc.) and lymphokines (IL-1, IL-2, etc.) have also been used as adjuvants and/or supplements to vaccine compositions and are contemplated within the scope of the present invention. One or more different cytokines and lymphokines can be included in a composition comprising an immunogen of the invention. In one embodiment, an immunogen of the invention is administered to an animal in combination with the lymphokine interleukin-12 (IL-12) in combination with another adjuvant. Also specifically contemplated within the scope of the invention is the use of the lymphokine interleukin-18 (IL-18) as part of an adjuvant composition. In one embodiment, an adjuvant composition used with the subject invention comprises a combination of IL-12 and IL-15, or IL-15 and IL-18, or IL-12 and IL-18, or IL-12, IL-15, and IL-18. Preferably, the cytokine is of a species that has biological activity in the feline animal. More preferably, the cytokine is a feline cytokine, e.g., feline IL-12, feline IL-15, feline IL-18, etc. In an exemplified embodiment, a primate derived immunogen is administered in combination with Ribi adjuvant system component including CWS and IL-12 and/or IL-18.

Abbreviations of FIV strains used herein are shown below:

| Strain (subtype) | Abbreviation |
|---|---|
| Petaluma (A) | $FIV_{Pet}$ |
| Dixon (A) | $FIV_{Dix}$ |
| UK8 (A) | $FIV_{UK8}$ |
| Bangston (B) | $FIV_{Bang}$ |

-continued

| Strain (subtype) | Abbreviation |
| --- | --- |
| Aomori-1 (B) | $FIV_{Aom1}$ |
| Aomori-2 (B) | $FIV_{Aom2}$ |
| Fc1 (B) | $FIV_{FC1}$ |
| Shizuoka (D) | $FIV_{Shi}$ |
| Dutch113 (A) | $FIV_{Dut113}$ |
| Dutch19K (A) | $FIV_{Dut19}$ |
| UK2 (A) | $FIV_{UK2}$ |
| SwissZ2 (A) | $FIV_{SwiZ2}$ |
| Sendai-1 (A) | $FIV_{Sen1}$ |
| Sendai-2 (B) | $FIV_{Sen2}$ |
| USCAzepy01A (A) | FIV |
| USCAhnky11A (A) | $FIV_{USC11}$ |
| USCAtt-10A (A) | $FIV_{USC10}$ |
| USCAlemy01 (A) | FIV |
| USCAsam-01A (A) | FIV |
| PPR (A) | $FIV_{PPR}$ |
| FranceWo | $FIV_{Fra}$ |
| Netherlands | $FIV_{Net}$ |
| USILbrny03B (B) | $FIV_{USI03}$ |
| TM2 (B) | $FIV_{TM2}$ |
| USCKlgri02B (B) | $FIV_{USC02}$ |
| Yokohama (B) | $FIV_{Yok}$ |
| USMAsboy03B (B) | $FIV_{USMA03}$ |
| USTXmtex03B (B) | $FIV_{UST03}$ |
| USMCglwd03B (B) | $FIV_{USMC03}$ |
| CABCpbar03C (C) | $FIV_{CAB03}$ |
| CABCpbar07C (C) | $FIV_{CAB07}$ |
| CABCpady02C (C) | $FIV_{CAB02}$ |
| Fukuoka (D) | $FIV_{Fuku}$ |

The subject invention also concerns methods of use of an animal model for selecting for epitopes conserved between immunodeficiency viruses, such as HIV and FIV, that can be used to immunize a person or animal against infection by an immunodeficiency virus. In one embodiment of the method, HIV is isolated from an HIV-infected, long-term nonprogressor patient. As used herein, the term "long-term nonprogressors" refers to HIV-infected patients that exhibit a stable CD4 count for at least 10 years, exhibit a low virus load (i.e., virus level in plasma is low to undetectable as measured by RT-PCR) and typically exhibit few or no disease symptoms. Immunogens from the isolated HIV are prepared and used to immunize a feline animal, such as a domestic cat. In one embodiment of the method, peptide fragments of an HIV protein are used as immunogens. Preferably, overlapping fragments that represent the full length of the HIV protein are prepared for use as immunogens. In one embodiment, different combinations of the peptide fragments are administered to different cats in order to identify those fragments that contain epitopes that provide the strongest prophylactic protection against FIV infection. Immunized cats are subsequently challenged with FIV. Immunogens that protect a cat against infection when challenged with FIV comprise evolutionarily conserved epitopes and can be used as immunogens to immunize humans, feline animals, and other mammals against infection by immunodeficiency viruses. Preferably, the immunogen protects a cat against infection by FIV of more than one subtype. Fragments of an immunogen comprising an evolutationarily conserved epitope can be prepared and tested using the subject method to further isolate the epitope. Fragments can also be sequenced to determine the primary amino acid sequence of the epitope. In a preferred embodiment, an immunogen comprising an evolutionarily conserved epitope selected using the subject method can be used to immunize a human against infection from HIV. In one embodiment of the method, the immunogen used to immunize cats is an HIV p24 protein, or an immunogenic fragment thereof. The subject invention also concerns evolutionarily conserved epitopes of immunodeficiency viruses identified using the subject method.

The subject invention also concerns methods for inducing an immune response in humans and other animals against immunogens, antigens, or viruses comprising epitopes that are evolutionarily conserved among immunodeficiency viruses, such as HIV and FIV. In one embodiment, an immunogen(s) or antigen(s) comprising one or more evolutionarily conserved epitope(s) from an immunodeficiency virus(es) identified by methods described herein is administered to a person or animal in an amount and for a duration sufficient to induce an immune response against the immunogen or antigen and any virus or cell displaying the immunogen or antigen. The immune response induced can be humoral or cell-mediated or both. In one embodiment for inducing an immune response against HIV, a human is administered an immunogen comprising an evolutionarily conserved epitope identified from an HIV. Immunogens contemplated within the scope of the invention include, but are not limited to, an HIV p24 protein, or an immunogenic fragment thereof. In one embodiment, an immunogen used in the present method comprises an HIV-$1_{UCD1}$ p24 protein, or an immunogenic fragment thereof.

The subject invention also concerns methods for protecting humans, and other animals, such as cats, against infection by immunodeficiency viruses, such as HIV and FIV. In one embodiment of the method, an effective amount of an immunogen(s) or antigen(s) comprising one or more evolutionarily conserved epitope(s) from an immunodeficiency virus(es) identified by methods described herein is administered to a person or animal for a duration sufficient to immunize a person or animal and provide the person or animal with some level of protection against infection by an immunodeficiency virus. In one embodiment for protection against HIV infection, a human is immunized with an immunogen comprising an evolutionarily conserved epitope identified from an HIV. Immunogens contemplated within the scope of the invention include, but are not limited to, an HIV p24 protein, or an immunogenic fragment thereof. In one embodiment, an immunogen used in the present method comprises an HIV-$1_{UCD1}$ p24 protein, or an immunogenic fragment thereof.

The immunogens are typically administered parenterally, by injection, for example, either subcutaneously, intraperitoneally, or intramuscularly. Other suitable modes of administration include oral or nasal administration. Usually, the immunogens are administered to a human or other animal at least two times, with an interval of one or more weeks between each administration. However, other regimens for the initial and booster administrations of the immunogens are contemplated, and may depend on the judgment of the practitioner and the patient being treated.

The immunogenic compositions of the subject invention can be prepared by procedures well known in the art. For example, the immunogens are typically prepared as injectables, e.g., liquid solutions or suspensions. The immunogens are administered in a manner that is compatible with dosage formulation, and in such amount as will be therapeutically effective and immunogenic in the recipient. The optimal dosages and administration patterns for a particular immunogens formulation can be readily determined by a person skilled in the art.

Immunogens that can be used in accordance with the present invention can be provided with a pharmaceutically-acceptable carrier or diluent. In one embodiment, an immunogen of the invention is provided with one or more adjuvants that increase the human or animal's immune response against the immunogen. Immunogens of the invention can be provided with and/or administered with any suitable adjuvant or adjuvants known in the art.

The subject invention also concerns compositions comprising an immunogen of the invention derived from a primate immunodeficiency virus and a feline cytokine or lymphokine. The immunogen can be from HIV, including HIV-1, e.g., HIV-1$_{IIIB}$, HIV-1$_{UCD1}$, and HIV-1$_{BRU}$, and HIV-2. HIV immunogens of the composition include, but are not limited to, HIV gp160, gp120, gp41, p24, p31, p17, p7 or a protein encoded by an HIV gag, pol, env, tat, rev, net, vif, vpr, vpu, or vpx genes, or a fragment or variant thereof. In one embodiment, the lymphokine is feline IL-12, IL-15, and or IL-18. In an exemplified embodiment, the immunogen is HIV-1 p24 and the lymphokine is feline IL-18. Compositions can also include an adjuvant, such as one of the adjuvants described herein.

The subject invention also concerns kits and dosage formulations comprising in one or more containers an immunogen of the invention derived from a primate immunodeficiency virus and a feline cytokine or lymphokine. The immunogen can be from HIV, including HIV-1, e.g., HIV-1$_{IIIB}$, HIV-1$_{UCD1}$, and HIV-1$_{BRU}$, and HIV-2. HIV immunogens of the composition include, but are not limited to, HIV gp160, gp120, gp41, p24, p31, or a protein encoded by an HIV gag, pot, env, tat, rev, lief vif vpr, vpu, or vpx gene, or a fragment or variant thereof In one embodiment, the lymphokine is feline IL-12, IL-15, and or IL-18. In an exemplified embodiment, the immunogen is HIV-1 p24 and the lymphokine is feline IL-18. Kits and dosage formulations can also include an adjuvant, such as one of the adjuvants described herein.

All patents, patent applications, provisional applications, and publications referred to or cited herein are incorporated by reference in their entirety to the extent they are not inconsistent with the explicit teachings of this specification.

Following are examples which illustrate procedures for practicing the subject invention. These examples should not be construed as limiting. All percentages are by weight and all solvent mixture proportions are by volume unless otherwise noted.

EXAMPLE 1

Four SPF cats each (n-4) were immunized four times with either HIV-1 vaccine formulation A or HIV-1 vaccine formulation B at 3 week intervals and challenged 3 weeks after the last boost with 15 cat infectious doses (CID$_{50}$) of in vivo-derived FIV$_{Bangston}$ innoculum. Additional four SPF cats (control group) received no immunization but were similarly challenged with FIV. HIV-1 vaccine formulation A consisted of 200 μg of HIV-1$_{UCD1}$ p24, 25 μg, of HIV-1$_{IIIB}$ gp120 (ImmunoDiagnostics Inc., Woburn, Mass.), and 25 μg of HIV-1$_{IIIB}$ gp160 (ImmunoDiagnostics Inc.) mixed in 0.5 ml of Ribi Adjuvant System comprising the cell wall skeleton (CWS) component (25 μg/dose cell wall skeleton)(Corixa Corp., Seattle, Wash.) containing 5 μg of recombinant human interleukin-12 (rHuIL-12). HIV-1 vaccine formulation B consisted of 200 μg of HIV-1$_{UCD1}$ p24 mixed in 0.5 ml of Ribi Adjuvant System CWS component containing 5 μg of rHuIL-12. Recombinant HIV-1$_{UCD1}$ p24 was produced in an *E. coli* expression system using QIAexpress pQE vector (Qiagen Inc., Valencia, Calif.) and the expressed 6xHis-tagged p24 product was purified by Ni-NTA affinity chromatography (Qiagen Inc.). In vivo-derived FIV innoculum consisted of pooled plasma from two FIV$_{Bangston}$-infected cats which was titrated in vivo using groups of 3-4 SPF cats per log$_{10}$ dilution (Pu et al., 2001).

Results of this study are shown in Table 1. As an additional method of determining FIV infection status, virus isolation was performed using both reverse transcriptase (RT) assay with proviral PCR as virus detection systems. One of four (¼) cats immunized with HIV-1 vaccine formulation A and two of four (2/4) cats immunized with HIV-1 vaccine formulation B and subsequently challenged with FIV were negative for FIV by virus isolate, lost antibodies to FIV p24 and developed no antibodies to FIV gp95 at 16 weeks post challenge, while the remaining cats developed antibodies to FIV gp95 and developed persistently stronger antibody responses to FIV p24. All four control cats developed antibodies to both FIV p24 and gp95 by 16 weeks post challenge and virus isolation positive for FIV by 13 weeks post challenge. Hence, HIV-1 vaccine formulation B (HIV-1 p24 alone) appeared to have better or equivalent efficacy at protecting cats against FIV challenge than HIV-1 vaccine formulation A, suggesting that HIV-1$_{UCD1}$ p24 is a vaccine component that can induce protective immunity against FIV challenge. All four cats immunized with HIV-1 vaccine formulation A and three of four cats immunized with HIV-1 vaccine formulation B developed cross-reactive antibodies to FIV p24 after the fourth (4th) vaccination.

Since there were no cross-reactive antibodies to FIV gp95 in HIV-1 vaccinated cats that exhibited a protective immune response to FIV, the absence or presence of antibodies to FIV gp95 was indicative of whether an animal had been vaccinated with HIV or infected with FIV, respectively. In addition, the loss of cross-reactive antibodies to FIV p24 in vaccinated cats by the end of the study was also indicative that the vaccinated animals were protected from FIV challenge.

EXAMPLE 2

In a subsequent study, four specific-pathogen-free (SPF) cats were each immunized with either HIV-1/UCD1 (HIV-1$_{UCD1}$) p24 or HIV-1/LAV (HIV-1$_{LAV}$) p24 vaccines at 250 μg/dose in 1 ml of Ribi adjuvant (25 μg/dose CWS (cell wall skeleton)) supplemented with 5 μg/dose of recombinant human IL-12 (rHuIL-12). An additional group of three SPF cats received HIV-1$_{UCD1}$ p24 without Ribi adjuvant or rHuIL-12 to evaluate the importance of adjuvant. A control group of cats received either Ribi adjuvant or PBS. All cats were immunized three (3) times at three (3) week intervals and challenged three (3) weeks after the last immunization with 15 CID$_{50}$ of in vivo-derived FIV-Bangston (FIV$_{Bang}$). As shown in Table 2, four of four (4/4) cats immunized with HIV-1$_{UCD1}$ p24 with adjuvant were protected from FIV infection at a dose where all four control cats were infected with FIV following challenge. The protected cats immunized with HIV-1$_{UCD1}$ p24 with adjuvant were negative for FIV infection as of 54 weeks post challenge and, therefore, they were completely protected. Results shown in Table 2 suggest that the HIV-1$_{UCD1}$ p24 vaccine (4 of 4 cats or 100% protected) is more effective than the HIV-1$_{LAV}$ p24 vaccine (2 of 4 cats or 50% protected). The group that received HIV-1$_{UCD1}$ p24 without adjuvant had minimal protection from infection when challenged with FIV (1 of 3 cats or 33% protected).

EXAMPLE 3

Another study was performed to determine whether the protection induced by HIV-1$_{LAV}$ p24 vaccine is reproducible. In this study, three SPF cats were immunized with 200 μg/dose of HIV-1$_{LAV}$ p24 vaccine formulated in 1 ml of Ribi adjuvant (25 μg/dose CWS (cell wall skeleton)) supplemented with 5 μg/dose of rHuIL-12. In addition, three SPF cats each were immunized with 200 μg/dose of either FIV$_{Bang}$ p24 or FIV-Petaluma+Shizuoka (FIV$_{pet/Shi}$) p24 vaccines formulated in Ribi adjuvant (25 μg/dose CWS (cell wall skeleton)) with 5 μg/dose of rHuIL-12. $FIV_{Pet/Shi}$ p24 vaccine consisted of 130 μg of $FIV_{pet}$ p24 and 70 μg of $FIV_{Shi}$ p24 in Ribi adjuvant supplemented with rHuIL-12. Three control cats received adjuvant. Immunization and challenge schedules including challenge innoculum and dose were the same as described in Example 2. As shown in Table 3, three of three (⅔) cats immunized with $HIV-1_{LAV}$ p24 vaccine were protected at a dose which infected all three control cats. Only 1 of 3 cats immunized with $FIV_{Bang}$ p24 vaccine and 2 of 3 cats immunized $FIV_{Pet/Shi}$ p24 vaccine were protected. These results confirm that the $HIV-1_{LAV}$ p24 vaccine is also effective as vaccine against FIV. Moreover, the HIV-1 p24 vaccine is as effective as the $FIV_{Pet/Shi}$ p24 vaccine and may be more effective than the $FIV_{Bang}$ p24 vaccine against $FIV_{Bang}$ challenge.

EXAMPLE 4

Another study was performed to evaluate the effect of lowering the p24 vaccine dose and changing the cytokine supplementation of the adjuvant. Three SPF cats were immunized with 200 μg/dose of p24 antigen formulated in 1 ml of Ribi adjuvant (25 μg/dose CWS (cell wall skeleton)) supplemented with recombinant feline IL-18 (rFeIL-18; 5 μg/dose) instead of rHuIL-12. In order to determine the effect of cytokine supplementation of the adjuvant, three additional SPF cats were immunized with 200 μg/dose of $HIV-1_{UCD1}$ p24 antigen formulated in Ribi adjuvant (25 μg/dose CWS (cell wall skeleton)) with no cytokine supplementation. As controls, two SPF cats each were immunized with either Ribi adjuvant with supplemented rFeIL-18, Ribi adjuvant alone, or PBS. Immunization and challenge schedules were the same as described in Examples 2 and 3 with the exception of the slightly higher challenge dose of 25 $CID_{50}$. As shown in Table 4, two of three (⅔) cats immunized with $HIV-1_{UCD1}$ p24 vaccine formulated in rFeIL-18 supplemented Ribi adjuvant were protected, whereas, only one of three (⅓) cats immunized HIV-1 p24 vaccine formulated with only Ribi adjuvant were protected. All control cats were infected by 5 to 9 weeks post challenge. Hence, protection (2 of 3 cats) was demonstrated with $HIV-1_{UCD1}$ p24 vaccine formulated in Ribi/FeIL-18. Furthermore, $HIV-1_{UCD1}$ p24 vaccine formulated in Ribi/FeIL-18 appeared to be more effective than the one formulated in only Ribi adjuvant (without FeIL-18) (2 of 3 protected cats vs. 1 of 3 protected cats).

EXAMPLE 5

In another study, the challenge strain was changed from $FIV_{Bang}$ (which is subtype A/B) to $FIV_{FC1}$ (which is subtype B) to test whether the HIV-1 p24 vaccine will protect cats against other FIV challenge strains. $FIV_{Bang}$ has group-specific antigen (gag), polymerase (pol), and small portion (V1-V3 regions) of the envelope (env) gene sequences belonging to subtype A, while a majority of the env gene (V4-V9 regions) belongs to subtype B. Hence, $FIV_{Bang}$ is a recombinant of subtypes A and B. On the other hand, $FIV_{FC1}$ has subtype B gene sequences at gag, pol, and env, and is completely a subtype B strain. The gag consists of matrix-core-nucleocapsid and the core gene is the gene for p24. Thus, $HIV-1_{UCD1}$ and $HIV-1_{LAV}$ p24 vaccines protected cats against $FIV_{Bang}$, which has a subtype A p24. This study tested whether the HIV-1 p24 vaccine protects cats against infection by $FIV_{FC1}$ which has a subtype B p24.

Four SPF cats were immunized with 200 mg/dose of $HIV-1_{UCD1}$ p24 in 1 ml of Ribi adjuvant (25 μg/dose CWS (cell wall skeleton)) supplemented with 5 μg/dose of rHuIL-12. For comparison, an additional four (4) SPF cats were immunized with a commercially available dual-subtype $FIV_{Pet/Shi}$ vaccine (FEL-O-VAX FIV; Forth Dodge Animal Health, Overland Park, Kans.) in the adjuvant supplied with the vaccine. Three control cats received immunization with PBS. The immunization and challenge schedules were the same as described in Examples 2 and 3 with the exception of the challenge innoculum of $FIV_{FC1}$ was 15 $CID_{50}$. As shown in the results in Table 5, three of four (¾) cats immunized with $HIV-1_{UCD1}$ p24 vaccine and all four FEL-O-VAX FIV-immunized cats were protected at a dose where all three control cats were infected. Hence, HIV-1 p24 vaccine protected cats against a challenge strain ($FIV_{FC1}$), which had subtype B p24 and is significantly different from the $FIV_{Bang}$ challenge strain.

EXAMPLE 6

The results from the studies described in Example 1 through Example 5 are summarized in Table 6. Overall, 11 of 15 (73.3%) cats immunized with $HIV-1_{UCD1}$ p24 formulated in Ribi/rHuIL-12 or Ribi/rFeIL-18 adjuvant were protected. Similarly, 5 of 7 (71.4%) cats immunized with $HIV-1_{LAV}$ p24 formulated in Ribi/rHuIL-12 were protected. Initial analysis of immunization with HIV-1 p24 formulated with only Ribi/rHuIL-12 indicate that $HIV-1_{UCD1}$ p24 vaccine (7 of 8 protected cats or 87% protection) may be more effective than $HIV-1_{LAV}$ p24 vaccine (5 of 7 protected cats or 71% protection). Nonetheless, full sterilizing protection was observed in a combined total of 16 of 22 (72.7%) cats immunized with HIV-1 p24 vaccines in Ribi/rHuIL-12 or Ribi/rFeIL-18, which was substantially higher in protection than the 3 of 6 (50%) cats protected after immunization with FIV p24 vaccine.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

HIV-1 Protein Immunogenicity & Efficacy Against $FIV_{Bang}$ Challenge Infection (Study 1)

| Cat # | VACCINE: HIV-1 Immunogens (Adjuvants) | FIV Immunoblot (p24/gp95) | | | | | | | HIV-1 Immunoblot (p24/gp120/160) | | FIV Status (Virus Isolation) | | | | FIV Status Summary |
|---|---|---|---|---|---|---|---|---|---|---|---|---|---|---|---|
| | | Pre | V3 | V4 | 4 wpc | 7 wpc | 10 wpc | 13 wpc | 16 wpc | Pre | V4 | 10 wpc | 13 wpc | 16 wpc | 18 wpc | |
| | Formulation A: | | | | | | | | | | | | | | | |
| L99 | $HIV-1_{UCD1}$ p24+ | −/− | −/H | +/H | ±/H | +/− | +/− | +/− | +/+ | −/− | +/+ | + | + | + | + | + |
| 808 | $HIV-1_{HIB}$ gp120/160 | −/− | ++/H | ++/H | +/H | +/− | +/− | +/− | +/+ | −/− | +/+ | + | + | + | + | + |

TABLE 1-continued

HIV-1 Protein Immunogenicity & Efficacy Against FIV$_{Bang}$ Challenge Infection (Study 1)

| Cat # | VACCINE: HIV-1 Immunogens (Adjuvants) | FIV Immunoblot (p24/gp95) | | | | | | | | HIV-1 Immunoblot (p24/gp120/160) | | FIV Status (Virus Isolation) | | | | FIV Status Summary |
|---|---|---|---|---|---|---|---|---|---|---|---|---|---|---|---|---|
| | | Pre | V3 | V4 | 4 wpc | 7 wpc | 10 wpc | 13 wpc | 16 wpc | Pre | V4 | 10 wpc | 13 wpc | 16 wpc | 18 wpc | |
| 9QM | | −/− | +/H | +/H | ±/− | −/− | −/− | −/− | −/− | −/− | +/+ | − | − | − | − | − |
| 902 | (Ribi + IL-12) | −/− | +/H | ++/H | +/H | +/− | +/− | +/− | +/+ | −/− | +/+ | + | + | + | + | + |
| | Formulation B: | | | | | | | | | | | | | | | |
| K99 | | −/− | −/− | −/− | −/− | −/− | −/− | −/− | −/− | −/− | +/− | − | − | − | − | − |
| 806 | HIV-1$_{UCD1}$ p24 | −/− | −/− | +/− | ±/− | +/− | +/− | +/− | +/+ | −/− | +/− | + | + | + | + | + |
| 9QL | | −/− | +/− | +/− | +/− | −/− | −/− | −/− | −/− | −/− | +/− | − | − | − | − | − |
| 901 | (Ribi + IL-12) | −/− | −/− | +/− | +/− | ±/− | +/− | +/− | +/+ | −/− | +/− | + | + | + | + | + |
| M99 | | −/− | −/− | −/− | +/− | +/− | +/− | +/− | +/+ | −/− | ND | + | + | + | + | + |
| 811 | None | −/− | −/− | −/− | +/− | +/− | +/− | +/± | +/+ | −/− | ND | + | + | + | + | + |
| 9QN | | −/− | −/− | −/− | ±/− | +/− | ±/− | ±/− | +/+ | −/− | ND | − | + | + | + | + |
| 6DJ | | −/− | −/− | −/− | +/+ | ±/− | +/+ | +/+ | +/+ | −/− | ND | + | + | + | + | + |

Pre = pre-vaccination; V3 = post-3rd vaccination; V4 = post-4th vaccination.

4, 7, 10, 13, 16 & 18 wpc = 4, 7, 10, 13, 16 and 18 weeks post-challenge with FIV.

Negative (−/−) for antibodies to core p24 and envelope (FIV gp95; HIV gp120/160).

Positive for p24 antibodies but not for envelope antibodies (+/−).

Positive (+/+) for antibodies to core p24 and envelope.

H = antibodies to high molecular weight (p70) protein but no antibodies to FIV envelope (gp95).

ND = not determined

TABLE 2

HIV-1 Protein Immunogenicity (3X Immunization) & Efficacy Against Subtype-A/B FIV$_{Bang}$ Challenge Infection (15 CID$_{50}$) (Study 2)

| Cat # | VACCINE: HIV-1 Immunogens (Adjuvants) | FIV Immunoblot (p24/gp95) | | | | | | | | FIV Status (Virus Isolation) | | | | | | FIV Status Summary |
|---|---|---|---|---|---|---|---|---|---|---|---|---|---|---|---|---|
| | | Pre | V3 | 4 wpc | 6 wpc | 9 wpc | 12 wpc | 16 wpc | 20 wpc | 4 wpc | 6 wpc | 9 wpc | 12 wpc | 16 wpc | 20/54 wpc | |
| G9F | HIV-1$_{UCD1}$ p24 | −/− | +/− | +/− | ±/− | −/− | −/− | −/− | −/− | − | − | − | − | − | −/− | − |
| P99 | 250 μg/dose | −/− | +/− | +/− | ±/− | −/− | −/− | −/− | −/− | − | − | − | − | − | −/− | − |
| 93M | | −/− | +/− | +/− | ±/− | −/− | −/− | −/− | −/− | − | − | − | − | − | −/− | − |
| 400 | (Ribi + IL-12) | −/− | +/− | +/− | ±/− | −/− | −/− | −/− | −/− | − | − | − | − | − | −/− | − |
| R99 | HIV-1$_{LAV}$ p24 | −/− | +/− | +/− | ±/− | −/− | −/− | −/− | −/− | − | − | − | − | − | −/− | − |
| 93P | 250 μg/dose | −/− | +/− | +/− | +/− | +/− | +/+ | +/+ | +/+ | − | + | + | + | + | +/T | + |
| DE1 | | −/− | +/− | +/− | +/− | +/− | +/+ | +/+ | +/+ | + | + | + | + | + | +/T | + |
| O99 | (Ribi + IL-12) | −/− | +/− | +/− | +/− | −/− | −/− | −/− | −/− | − | − | − | − | − | −/− | − |
| S99 | HIV-1$_{UCD1}$ p24 | −/− | −/− | −/− | +/− | +/− | +/+ | +/+ | +/+ | − | − | + | + | + | +/T | + |
| 206 | 250 μg/dose | −/− | −/− | −/− | +/− | +/− | +/+ | +/+ | +/+ | − | − | + | + | + | +/T | + |
| MN1 | (No Adjuvant) | −/− | −/− | −/− | −/− | −/− | −/− | −/− | −/− | − | − | − | − | − | −/− | − |
| G9H | | −/− | −/− | −/− | +/− | +/− | +/+ | +/+ | +/+ | − | + | + | + | + | +/T | + |
| N99 | (Ribi or PBS) | −/− | −/− | −/− | +/− | +/− | +/+ | +/+ | +/+ | + | + | + | + | + | +/T | + |
| G9E | | −/− | −/− | −/− | +/− | +/− | +/+ | +/+ | +/+ | − | − | − | + | + | +/T | + |
| NN1 | | −/− | −/− | −/− | −/− | −/− | −/− | +/± | +/+ | − | − | − | − | + | +/T | + |

Pre = pre-vaccination; V3 = post-3rd vaccination; 4, 6, 9, 16, 20, 48, and 54 wpc = 4, 6, 9, 16, 20, 48, and 54 wk post-challenge with in vivo inoculum (pooled infected plasma) of FIV-Bang (subtype A/B). Ribi + IL-12 consist of Ribi adjuvant with 25 μg/dose cell wall skeleton and 5 μg of human IL-12 per dose.
FIV immunoblot negative (−/−) for antibodies to core p24 and envelope (FIV gp95) indicates still negative for FIV infection. FIV immunoblot positive for p24 antibodies but not for envelope antibodies (+/−). The vaccinated cat may be still negative for virus infection unless the anti-p24 antibody titer is stronger than previous titer. However, for PBS controls, such immunoblot reactivity will indicate FIV infection. FIV immunoblot positive (+/+) for antibodies to core p24 and envelope indicates positive for FIV infection in both vaccinated groups and PBS control group.
FIV virus isolation negative (−) and positive (+) were based on RT and PCR. FIV virus isolation negative at 20/54 wpc (−/−) represent isolation performed at 20 wpc and 54 wpc. These animals are still alive and will be used for 1-yr boost-challenge study. FIV virus isolation positive at 20 wpc but not tested at 48 wpc due to euthanasia of these animals after harvesting the tissues on 20 wpc (+/T).

TABLE 3

HIV-1 & FIV p24 Protein Immunogenicity (3x Immunization) & Efficacy
Against Subtype-A/B FIV$_{Bang}$ Challenge Infection (15 CID$_{50}$) (Study 3)

| Cat # | VACCINE: HIV-1 Immunogens (Adjuvants) | FIV Immunoblot (p24/gp95) | | | | | | | | FIV Status (Virus Isolation) | | | | | | | FIV Status Summary |
|---|---|---|---|---|---|---|---|---|---|---|---|---|---|---|---|---|---|
| | | Pre | V3 | 5 wpc | 8 wpc | 10 wpc | 12 wpc | 15 wpc | 18 wpc | 5 wpc | 8 wpc | 10 wpc | 12 wpc | 15 wpc | 18 wpc | | |
| 626 | HIV-1$_{LAV}$ p24 | −/− | +/− | +/− | −/− | −/− | −/− | −/− | −/− | − | − | − | − | − | −/− | | − |
| 637 | 200 µg/dose | −/− | +/− | +/− | −/− | −/− | −/− | ND | ND | − | − | − | − | ND | ND | | − |
| ID4 | (Ribi + IL-12) | −/− | +/− | +/− | −/− | −/− | −/− | −/− | −/− | − | − | − | − | − | −/− | | − |
| 628 | None | −/− | −/− | −/− | −/− | −/− | +/+ | +/+ | +/+ | − | − | − | − | − | + | | + |
| 633 | | −/− | −/− | −/− | −/− | −/− | +/+ | +/+ | +/+ | − | − | − | − | − | + | | + |
| ID2 | (Ribi/IL-12) | −/− | −/− | −/− | −/− | −/− | +/+ | +/+ | +/+ | + | + | + | + | + | + | | + |
| 631 | FIV$_{Bang}$ p24 | −/− | +/− | +/− | +/− | +/− | +/− | +/− | +/− | − | − | − | − | − | − | | − |
| 635 | 200 µg/dose | −/− | +/− | +/− | +/− | +/− | +/+ | +/+ | +/+ | − | − | − | + | − | + | | + |
| ID3 | (Ribi + IL-12) | −/− | +/− | +/− | +/− | +/+ | +/+ | +/+ | +/+ | + | + | + | + | + | + | | + |
| 630 | FIV$_{Pet/Shi}$ p24 | −/− | +/− | +/− | +/− | +/− | +/− | +/− | +/− | − | − | − | − | − | − | | − |
| ID1 | 200 µg/dose | −/− | +/− | +/− | +/− | +/+ | +/+ | +/+ | +/+ | + | + | + | + | + | + | | + |
| G9B | (Ribi + IL-12) | −/− | +/− | +/− | +/− | +/− | +/− | +/− | +/− | − | − | − | − | − | − | | − |

Pre = pre-vaccination; V3 = post-3rd vaccination; 5, 8, 10, 12, 15, and 18 wpc = 5, 8, 10, 12, 15, 18 wk post-challenge with in vivo inoculum (pooled infected plasma) of FIV-Bang. Ribi + IL-12 consist of Ribi adjuvant with 25 µg/dose cell wall skeleton and µg of human IL-12 per dose.
FIV immunoblot negative (−/−) for antibodies to core p24 and envelope (FIV gp95) indicates still negative for FIV infection. FIV immunoblot positive for p24 antibodies but not for envelope antibodies (+/−). The vaccinated cat may be still negative for virus infection unless the anti-p24 antibody titer is stronger than previous titer. However, for PBS controls, such immunoblot reactivity will indicate FIV infection. FIV immunoblot positive (+/+) for antibodies to core p24 and envelope indicates positive for FIV infection in both vaccinated groups and PBS control group.
FIV virus isolation negative (−) and positive (+) were based on RT and PCR. FIV immunoblot and virus isolation missing (ND = not done) for cat #637 due to accidental death after harvesting samples caused by reaction to anesthesia.

TABLE 4

HIV-1 p24 Protein Immunogenicity (3x Immunization & FeIL-18 adjuvant)
& Efficacy Against subtype-A/B FIV$_{Bang}$ Challenge (25 CID$_{50}$)(Study 4)

| Cat # | VACCINE: HIV-1 Immunogens (Adjuvants) | FIV Immunoblot (p24/gp95) | | | | | | FIV Status (Virus Isolation) | | | | FIV Status Summary |
|---|---|---|---|---|---|---|---|---|---|---|---|---|
| | | Pre | V3 | 5 wpc | 7 wpc | 9 wpc | 12-19 wpc | 5 wpc | 7 wpc | 9 wpc | 12-19 wpc | |
| IZ1 | HIV-1$_{UCD1}$ p24 | −/− | +/− | +/− | −/− | +/− | +/+ | + | + | + | + | + |
| JB6 | 200 µg/dose | −/− | +/− | +/− | −/− | −/− | −/− | − | − | − | − | − |
| IW1 | (Ribi + FeIL-18) | −/− | +/− | +/− | −/− | −/− | −/− | − | − | − | − | − |
| IZ3 | HIV-1$_{UCD1}$ p24 | −/− | +/− | +/− | −/− | −/− | −/− | − | − | − | − | − |
| JB5 | 200 µg/dose | −/− | +/− | +/− | +/− | +/− | +/+ | + | + | + | + | + |
| JA1 | (Ribi) | −/− | +/− | +/− | +/− | +/− | +/+ | + | + | + | + | + |
| IZ6 | | −/− | −/− | −/− | −/− | +/− | +/+ | − | − | + | + | + |
| JB2 | None | −/− | −/− | +/− | +/− | +/− | +/+ | + | + | + | + | + |
| IW2 | | −/− | −/− | −/− | +/− | +/− | +/+ | − | + | + | + | + |
| JJ4 | (Ribi + FeIL-18 or Ribi) | −/− | −/− | −/− | +/− | +/− | +/+ | − | − | + | + | + |
| JB1 | None | −/− | −/− | −/− | +/− | +/− | +/+ | − | − | + | + | + |
| MK2 | (PBS) | −/− | −/− | −/− | −/− | +/− | +/+ | − | − | + | + | + |

Pre = pre-vaccination; V3 = post-3rd vaccination; 5, 7, 9, and 12 wpc = 5, 7, 9, 12, 16, and 19 wk post-challenge with in vivo inoculum (pooled infected plasma) of FIV-Bang. Ribi + FeIL-18 consist of Ribi adjuvant with 25 µg/dose cell wall skeleton and 5 µg of feline IL-18 per dose.
FIV immunoblot negative (−/−) for antibodies to core p24 and envelope (FIV gp95) indicates still negative for FIV infection. FIV immunoblot positive for p24 antibodies but not for envelope antibodies (+/−). The vaccinated cat may be still negative for virus infection unless the anti-p24 antibody titer is stronger than previous titer. However, for PBS controls, such immunoblot reactivity will indicate FIV infection. FIV immunoblot positive (+/+) for antibodies to core p24 and envelope indicates positive for FIV infection in both vaccinated groups and PBS control group.
FIV virus isolation negative (−) and positive (+) were based on RT and PCR.

TABLE 5

HIV-1 p24 Protein Immunogenicity (3x Immunization) & Efficacy
Against subtype-B FIV$_{FC1}$ Challenge Infection (15 CID$_{50}$) (Study 5)

| Cat # | VACCINE: HIV-1 Immunogens (Adjuvants) | FIV Immunoblot (p24/gp95) | | | | | | FIV Status (Virus Isolation) | | | | FIV Status Summary |
|---|---|---|---|---|---|---|---|---|---|---|---|---|
| | | Pre | V3 | 5 wpc | 7 wpc | 9 wpc | 12-16 wpc | 5 wpc | 7 wpc | 9 wpc | 12-16 wpc | |
| AA1 | HIV-1$_{UCD1}$ p24 | −/− | +/− | +/− | −/− | +/− | +/+ | − | + | + | + | + |
| MD1 | 200 µg/dose | −/− | +/− | +/− | −/− | −/− | −/− | − | − | − | − | − |
| MG1 | | −/− | +/− | +/− | −/− | −/− | −/− | − | − | − | − | − |
| MF3 | (Ribi + IL-12) | −/− | +/− | +/− | −/− | −/− | −/− | − | − | − | − | − |
| AA2 | | −/− | +/+ | +/± | +/± | +/± | +/± | − | − | − | − | − |
| MD2 | Fel-O-Vax FIV$_{Pet/Shi}$ | −/− | +/+ | +/± | +/± | +/± | +/± | − | − | − | − | − |
| MG2 | | −/− | +/+ | +/± | +/± | +/± | +/± | − | − | − | − | − |
| MF4 | Fort Dodge adjuvant | +/+ | +/± | +/± | +/± | +/± | +/± | − | − | − | − | − |
| MD3 | None | −/− | −/− | −/− | −/− | +/− | +/+ | − | − | − | + | + |

TABLE 5-continued

HIV-1 p24 Protein Immunogenicity (3x Immunization) & Efficacy
Against subtype-B FIV$_{FC1}$ Challenge Infection (15 CID$_{50}$) (Study 5)

| Cat # | VACCINE: HIV-1 Immunogens (Adjuvants) | Pre | V3 | FIV Immunoblot (p24/gp95) 5 wpc | 7 wpc | 9 wpc | 12-16 wpc | FIV Status (Virus Isolation) 5 wpc | 7 wpc | 9 wpc | 12-16 wpc | FIV Status Summary |
|---|---|---|---|---|---|---|---|---|---|---|---|---|
| MG5 |  | −/− | −/− | −/− | −/− | +/− | +/+ | − | − | + | + | + |
| MK4 | (PBS) | −/− | −/− | −/− | −/− | +/− | +/+ | − | − | + | + | + |

Pre = pre-vaccination; V3 = post-3rd vaccination; 5, 7, 9, and 12 wpc = 5, 7, 9, 12, and 16 wk post-challenge with in vivo inoculum (pooled infected plasma) of FIV-FC1 (subtype B). Ribi + IL-12 consist of Ribi adjuvant with 25 µg/dose cell wall skeleton and 5 µg of human IL-12 per dose.
FIV immunoblot negative (−/−) for antibodies to core p24 and envelope (FIV gp95) indicates still negative for FIV infection. FIV immunoblot positive for p24 antibodies but not for envelope antibodies (+/−). The vaccinated cat may be still negative for virus infection unless the anti-p24 antibody titer is stronger than previous titer. However, for PBS controls, such immunoblot reactivity will indicate FIV infection. FIV immunoblot positive (+/±) for antibodies to core p24 and envelope indicates antibodies from vaccine in Fel-O-Vax FIV group and these cats are not infected. FIV immunoblot positive (+/+) for antibodies to core p24 and envelope indicates positive for FIV infection in both vaccinated groups and PBS control group.
FIV virus isolation negative (−) and positive (+) were based on RT and PCR.

TABLE 6

Summary Table

| p24 Vaccine | Adjuvant | Vaccination Frequency | Protection Rate (reference Table) | Individual Protection Rate | Combined Protection Rate |
|---|---|---|---|---|---|
| HIV-1/UCD1 p24 | Ribi + IL-12 | 3X | 4/4 (Table 2) 3/4 (Table 5) | 7/8 (87%) | 11/15 (73%) |
| HIV-1/UCD1 p24 | Ribi + IL-12 | 4X | 2/4 (Table 1) | 2/4 (50%) |  |
| HIV-1/UCD1 p24 | Ribi + FeIL-18 | 3X | 2/3 (Table 4) | 2/3 (67%) |  |
| HIV-1/LAV p24 | Ribi + IL12 | 3X | 2/4 (Table 2) 3/3 (Table 3) | 5/7 (71%) | 5/7 (71%) |
| FIV-Bang p24 | Ribi + IL-12 | 3X | 1/3 (Table 3) | 1/3 (33%) | 3/6 (50%) |
| FIV-Pet/Shi p24 | Ribi + IL-12 | 3X | 2/3 (Table 3) | 2/3 (67%) |  |

References

U.S. Pat. No. 6,503,753
U.S. Pat. No. 6,500,623
U.S. Pat. No. 5,846,825
U.S. Pat. No. 6,254,872
U.S. Pat. No. 6,447,993
U.S. Pat. No. 5,530,101
U.S. Pat. No. 5,763,160
U.S. Pat. No. 5,585,089
U.S. Pat. No. 5,693,762
U.S. Pat. No. 6,180,370
U.S. Pat. No. 6,407,213
U.S. Pat. No. 5,700,469
U.S. Pat. No. 5,401,628
U.S. Pat. No. 5,849,533
U.S. Pat. No. 5,846,546
U.S. Pat. No. 5,118,602
U.S. Pat. No. 5,565,319
U.S. Pat. No. 5,510,106
U.S. Pat. No. 5,275,813
U.S. Pat. No. 5,037,753
U.S. Pat. No. 4,861,720
U.S. Published Patent Application No. 20040076632
U.S. Published Patent Application No. 20040047878
U.S. Published Patent Application No. 20040009941
U.S. Published Patent Application No. 20020156037
U.S. Published Patent Application No. 20020032165
U.S. Published Patent Application No. 20010004531
Posnett, D. N. et al. (1988) "A Novel Method for Producing Anti-peptide Antibodies" *J. Biol. Chem.* 263(4):1719-1725.
Tam, J. P. (1988) "Synthetic Peptide Vaccine Design: Synthesis and Properties of a High-Density Multiple Antigenic Peptide System" *PNAS USA* 85(15):5409-5413.
Byars, N. E., A. C. Allison (1987) "Adjuvant formulation for use in vaccines to elicit both cell-mediated and humoral immunity," *Vaccine* 5:223-228.
Pedersen, N. C., E. W. Ho, M. L. Brown, J. K. Yamamoto (1987) "Isolation of a T-lymphotropic virus from domestic cats with an immunodeficiency-like syndrome," *Science* 235:790-793.
Yamamoto, J. K., N. C. Pedersen, E. W. Ho, T. Okuda, G. H. Theilen (1988a) "Feline immunodeficiency syndrome—a comparison between feline T-lymphotropic lentivirus and feline leukemia virus," *Leukemia*, December Supplement 2:204S-215S.
Yamamoto, J. K., E. Sparger, E. W. Ho, P. H. Andersen, T. P. O'Connor, C. P. Mandell, L. Lowenstine, N. C. Pedersen (1988b) "Pathogenesis of experimentally induced feline immunodeficiency virus infection in cats," *Am. J. Vet. Res.* 49:1246-1258.
Ackley, C. D., J. K. Yamamoto, N. B. Levy, N. C. Pedersen, M. D. Cooper (1990) "Immunologic abnormalities in pathogen-free cats experimentally infected with feline immunodeficiency virus," *J. Virol.* 64:5652-5655.
Olmsted, R. A., A. K. Barnes, J. K. Yamamoto, V. M. Hirsch, R. H. Purcell, P. R. Johnson (1989a) "Molecular cloning of feline immunodeficiency virus," *Proc. Nat. Acad. Sci.* 86:2448-2452.
Olmsted, R. A., V. M. Hirsch, R. H. Purcell, P. R. Johnson (1989b) "Nucleotide sequence analysis of feline immunodeficiency virus: Genome organization and relationship to other lentivirus," *Proc. Natl. Acad. Sci. USA* 86:8088-8092.
Talbott, R. L., E. E. Sparger, K. M. Lovelace, W. M. Fitch, N. C. Pedersen, P. A. Luciw, J. H. Elder (1989) "Nucleotide sequence and genomic organization of feline immunodeficiency virus," *Proc. Natl. Acad. Sci. USA* 86:5743-5747.

Hosie, M. J., O. Jarrett (1990) "Serological responses of cats to feline immunodeficiency virus," *AIDS* 4:215-220.

Sodora, D. L., E. G. Shpaer, B. E. Kitchell, S. W. Dow, E. A. Hoover, J. I. Mullins (1994) "Identification of three feline immunodeficiency virus (FIV) env gene subtype and comparison of the FIV and human immunodeficiency virus type 1 evolutionary patterns," *J. Virol.* 68:2230-2238.

Rigby, M. A., E. C. Holmes, M. Pistello, A. Mackay, A. J. Leigh-Brown, J. C. Neil (1993) "Evolution of structural proteins of feline immunodeficiency virus: molecular epidemiology and evidence of selection for change," *J. Gen. Virol.* 74:425-436.

Kakinuma, S., K. Motokawa, T. Hohdatsu, J. K. Yamamoto, H. Koyama, H. Hashimoto (1995) "Nucleotide Sequence of Feline Immunodeficiency Virus: Classification of Japanese Isolates into Two Subtypes Which Are Distinct from Non-Japanese Subtypes," *Journal of Virology* 69(6):3639-3646.

Murphy, F., D. W. Kingsbury (1990) "Virus Taxonomy," In *Fields Virology,* 2nd Ed., B. N. Fields, D. M. Knipe et al., eds, Raven Press, New York, Chapter 2, pp. 9-36.

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) "Phylogenetic analysis of gag genes from 70 international HIV-1 isolates provides evidence for multiple genotypes," *AIDS* 7:769-780.

Merrifield, R. B. (1963) "Solid Phase Peptide Synthesis. I. The Synthesis of a Tetrapeptide" *J. Amer. Chem. Soc.* 85:2149-2156.

Pu, R., J. Coleman, M. Omori, M. Mison, C. Huang, M. Arai, T. Tanabe, J. K. Yamamoto (2001) "Dual-subtype FIV vaccine protects cats against in vivo swarms of both homologous and heterologous subtype FIV isolates" *AIDS* 15:1-13.

Martin, E. W. (1995) *Remington's Pharmaceutical Science,* Easton Pa. Mack Publishing Company, 19$^{th}$ ed., 1995.

Whetter, L. E. et al. (1999) "Pathogenesis of simian immunodeficiency virus infection" *Journal of General Virology* 80:1557-1568.

Feigner, T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U.S.A.* 84(21): 7413-7417.

---

I claim:

1. A method for inhibiting infection by feline immunodeficiency virus (FIV) strain Bangston or strain FC1 in a feline animal, said method comprising administering to said animal the p24 polypeptide of human immunodeficiency virus type 1(HIV-1) strain UCD1 or LAV.

2. The method of claim 1, wherein said method further comprises administering an FIV immunogen subsequent to the administration of said HIV-1 p24 polypeptide.

3. The method of claim 1, wherein said polypeptide is administered with a pharmaceutically acceptable carrier or diluent.

4. The method of claim 1, wherein said polypeptide is administered with one or more adjuvants that increase the immune response of said animal against said polypeptide.

5. The method of claim 1, wherein said polypeptide is administered subcutaneously, intraperitoneally, intramuscularly, orally, or nasally.

6. The method of claim 4, wherein said adjuvant is selected from the group consisting of cytokine or lymphokine, threonyl muramyl dipeptide (MDP), Ribi Adjuvant System including cell wall skeleton (CWS), Freund's complete adjuvant, Freund's incomplete adjuvant, alum, aluminum hydroxide, and saponin.

7. The method of claim 6, wherein said cytokine or lymphokine is a feline cytokine or lymphokine.

8. The method of claim 1, wherein said polypeptide is administered in combination with interleukine-12, interleukin-15, or interleukin-18.

9. A method for inducing or generating an immune response against feline immunodeficiency virus in a feline animal, said method comprising administering to said animal the p24 polypeptide of human immunodeficiency virus type 1(HIV-1) strain UCD1 or LAV.

10. The method according to claim 9, wherein said immune response is a cellular immune response.

11. The method according to claim 9, wherein said immune response is a humoral immune response.

12. The method of claim 9, wherein said method further comprises administering an FIV immunogen subsequent to the administration of said HIV-1 p24 polypeptide.

13. The method of claim 9, wherein said polypeptide is administered with a pharmaceutically acceptable carrier or diluent.

14. The method of claim 9, wherein said polypeptide is administered with one or more adjuvants that increase the immune response of said animal against said polypeptide.

15. The method of claim 9, wherein said polypeptide is administered subcutaneously, intraperitoneally, intramuscularly, orally, or nasally.

16. The method of claim 14, wherein said adjuvant is selected from the group consisting of cytokine or lymphokine, threonyl muramyl dipeptide (MDP), Ribi Adjuvant System including cell wall skeleton (CWS), Freund's complete adjuvant, Freund's incomplete adjuvant, alum, aluminum hydroxide, and saponin.

17. The method of claim 16, wherein said cytokine or lymphokine is a feline cytokine or lymphokine.

18. The method of claim 9, wherein said polypeptide is administered in combination with interleukine-12, interleukin-15, or interleukin-18.

19. The method of claim 1, wherein said polypeptide is administered with Ribi Adjuvant System with cell wall skeleton and human IL-12 or feline IL-18.

20. The method of claim 9, wherein said polypeptide is administered with Ribi Adjuvant System with cell wall skeleton and human IL-12 or feline IL-18.

* * * * *

UNITED STATES PATENT AND TRADEMARK OFFICE
CERTIFICATE OF CORRECTION

PATENT NO. : 8,703,145 B2
APPLICATION NO. : 12/575058
DATED : April 22, 2014
INVENTOR(S) : Janet K. Yamamoto It is certified that error appears in the above-identified patent and that said Letters Patent is hereby corrected as shown below:

In The Specification

Column 1,
Lines 33-34, "Characteristics of
FIV have" should read --Characteristics of FIV have--.

Column 6,
Line 19, "cells arc" should read --cells are--.
Line 24, "Lek promoter," should read --Lck promoter,--.

Column 7,
Line 1, "(Feigner" should read --(Felgner--.

Column 8,
Line 55, "invention, in" should read --invention. In--.

Column 12,
Line 18, "thereof In" should read --thereof. In--.

Column 13,
Line 8, "net," should read --nef,--.
Line 23, "pot, env, tat, rev, lief vif vpr," should read --pol, env, tat, rev, nef, vif, vpr,--.
Line 24, "thereof In" should read --thereof. In--.

Column 15,
Line 22, "of p24" should read --of HIV-1$_{UCD1}$ p24--.
Line 66, "HIV-1$_{HIB}$" should read --HIV-1$_{IIIB}$--.

Signed and Sealed this
Twenty-eighth Day of April, 2015

Michelle K. Lee
*Director of the United States Patent and Trademark Office*

Column 17,
Line 59, "-/-" should read -- -/- --.

Column 24,
Line 19, "Feigner, T. R." should read --Felgner, P.L., T.R.--.